United States Patent [19]

Sasaki

[11] Patent Number: 4,892,949

[45] Date of Patent: * Jan. 9, 1990

[54] STILBENE DERIVATIVES

[75] Inventor: Masaomi Sasaki, Susono, Japan

[73] Assignee: Ricoh Company, Ltd., Tokyo, Japan

[*] Notice: The portion of the term of this patent subsequent to May 7, 2002 has been disclaimed.

[21] Appl. No.: 230,320

[22] Filed: Aug. 9, 1988

Related U.S. Application Data

[60] Division of Ser. No. 875,510, Jun. 18, 1986, which is a continuation of Ser. No. 488,883, Apr. 26, 1983, abandoned.

[30] Foreign Application Priority Data

| Apr. 30, 1982 | [JP] | Japan | 57-73075 |
| Apr. 30, 1982 | [JP] | Japan | 57-73076 |
| May 14, 1982 | [JP] | Japan | 57-80115 |
| May 14, 1982 | [JP] | Japan | 57-80116 |

[51] Int. Cl.$^4$ ............... C07D 211/08; C07D 211/20; C07D 209/82; C07D 95/08

[52] U.S. Cl. ..................... 546/98; 546/192; 546/236; 548/440; 564/315; 564/319

[58] Field of Search ............. 564/319, 315; 546/98, 546/192, 236; 548/440

[56] References Cited

U.S. PATENT DOCUMENTS

| 3,759,928 | 9/1973 | Zivkovic | 546/192 |
| 4,104,383 | 8/1978 | Krausz | 546/192 |
| 4,202,894 | 5/1980 | Pfiffner | 546/192 |
| 4,241,058 | 12/1980 | Pfiffner | 546/192 |
| 4,515,883 | 5/1985 | Sasaki | 430/58 |
| 4,521,605 | 6/1985 | Okazaki et al. | 548/440 |
| 4,603,097 | 7/1986 | Shoshi et al. | 430/73 |
| 4,619,881 | 10/1986 | Makino et al. | 546/98 |
| 4,695,631 | 9/1987 | Otsuka et al. | 546/192 |
| 4,709,096 | 11/1987 | Sasaki | 564/374 |
| 4,814,453 | 3/1989 | Shinzel et al. | 546/98 |

FOREIGN PATENT DOCUMENTS

| 2202895 | 8/1972 | Fed. Rep. of Germany | 546/98 |
| 167383 | 12/1981 | Japan | 546/98 |

Primary Examiner—Glennon H. Hollrah
Assistant Examiner—Raymond Covington
Attorney, Agent, or Firm—Flynn, Thiel, Boutell & Tanis

[57] ABSTRACT

An electrophotograhic photoconductor is disclosed which comprises an electroconductive support material and a photosensitive layer comprising at least one of the stilbene compounds of the formula

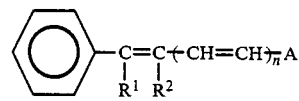

wherein R$^1$ represents hydrogen or

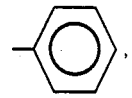

R$^2$ represents hydrogen, an alkyl group or a substituted or unsubstituted phenyl group; A represents

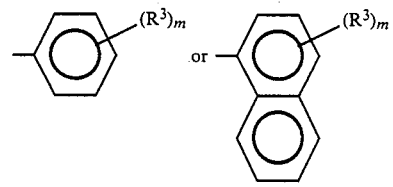

when R$^1$ is hydrogen; while when R$^1$ is A represents (Abstract continued on next page.)

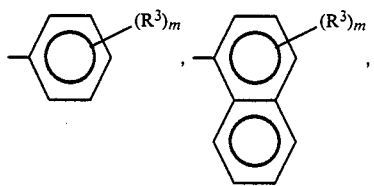

a 9-anthryl group or a substituted or unsubstituted N-alkylcarbazolyl group, wherein $R^3$ represents hydrogen, an alkyl group, an alkoxy group, a halogen or a substituted amino group represented by

in which $R^4$ and $R^5$ independently represent an alkyl group, a substituted or unsubstituted aryl group, or a substituted or unsubstituted aralkyl group, and $R^4$ and $R^5$ may form a ring in combination, and m is an integer of 0 through 3 and n is an integer of 0 or 1, provided that, when $R^1$ is hydrogen and n=0, A is

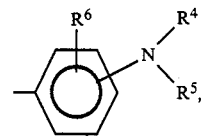

in which $R^6$ is hydrogen, an alkyl group, an alkoxy group or a halogen, and $R^4$ and $R^5$ are the same as defined above.

13 Claims, 8 Drawing Sheets

STILBENE DERIVATIVES

This is a division of Ser. No. 875,510, filed June 18, 1986, which is a continuation of Ser. No. 488,883, filed Apr. 26, 1983, now abandoned.

BACKGROUND OF THE INVENTION

The present invention relates to an electrophotographic photoconductor, and more particularly to an electrophotographic photoconductor comprising a photosensitive layer containing a novel stilbene compound overlayed on an electroconductive support material.

Conventionally, a variety of inorganic and organic electrophotographic photoconductors are known. As inorganic photoconductors for use in electrophotography, these are known types, in which the photoconductive material is, for instance, selenium, cadmium sulfide, and zinc oxide. In an electrophotographic process, a photoconductor is first exposed to corona charges in the dark, so that the surface of the photoconductor is electrically charged uniformly. The thus uniformly charged photoconductor is then exposed to original light images and the portions exposed to the original light images selectively become electroconductive so that the electric charges dissipate from the exposed portions of the photoconductor, whereby latent electrostatic images corresponding to the original light images are formed on the surface of the photoconductor. The latent electrostatic images are then developed by the so-called toner which comprises a colorant, such as a dye or a pigment, and a binder agent made, for instance, of a polymeric material; thus, visible developed images can be obtained on the photoconductor. It is necessary that photoconductors for use in electrophotography have at least the following fundamental properties: (1) chargeability to a predetermined potential in the dark; (2) minimum electric charge dissipation in the dark; and (3) quick dissipation of electric charges upon exposure to light.

While the above-mentioned inorganic electrophotographic photoconductors have many advantages over other conventional electrophotographic photoconductors, at the same time they have several shortcomings from the viewpoint of practical use.

For instance, a selenium photoconductor, which is widely used at present, has the shortcoming that its production is difficult and, accordingly, its production cost is high. Further, it is difficult to work it into the form of a belt due to its poor flexibility, and it is so vulnerable to heat and mechanical shocks that it must be handled with the utmost care.

Cadmium sulfide photoconductors and zinc oxide photoconductors are prepared by dispersing cadmium sulfide or zinc oxide in a binder resin. They can be produced inexpensively compared with selenium photoconductors and are also used commonly in practice. However, the cadmium sulfide and zinc oxide photoconductors are poor in surface smoothness, hardness, tensile strength and wear resistance. Therefore, they are not suitable as photoconductors for use in plain paper copiers in which the photoconductors are used in quick repetition.

Recently, organic electrophotographic photoconductors, which are said not to have the such shortcomings of the inorganic electrophotographic photoconductors, have been proposed, and some of them are in fact employed for practical use. Representative examples of such organic electrophotographic photoconductors are an electrophotographic photoconductor comprising poly-N-vinylcarbazole and 2,4,7-trinitro-fluorene-9-one (U.S. Pat. No. 3,484,237); a photoconductor in which poly-N-vinylcarbazole is sensitized by a pyrylium salt type coloring material (Japanese Patent Publication No. 48-25658); a photoconductor containing as the main component an organic pigment (Japanese Laid-Open patent application No. 47-37543); and a photoconductor containing as the main component an eutectic crystaline complex (Japanese Laid-Open patent application No. 47-10735).

Although the above-mentioned organic electrophotographic photoconductors have many advantages over other conventional electrophotographic photoconductors, they still have several shortcomings from the viewpoint of practical use, in particular, for use in high speed copying machines, in terms of cost, production, durability and electrophotographic sensitivity.

SUMMARY OF THE INVENTION

It is therefore an object of the present invention to provide an electrophotographic photoconductor or element comprising a photoconductor layer containing a novel stilbene compound and an electroconductive support material for supporting the photoconductive layer thereon, with high photosensitivity and uniform spectral absorption in the visible region, which does not give rise to difficulties in producing the electrophotographic photoconductor, and which is comparatively inexpensive and excellent in durability.

The stilbene compound employed in the present invention is represented by the following general formula:

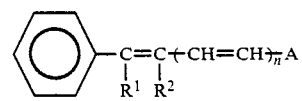

wherein $R^1$ represents hydrogen or

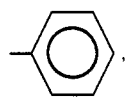

$R^2$ represents hydrogen, an alkyl group or a substituted or unsubstituted phenyl group; A represents

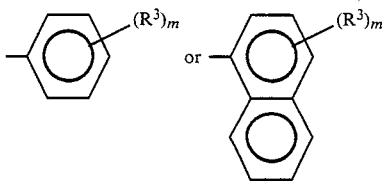

when R[1] is hydrogen; while, when R[1] is

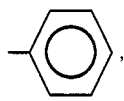

A represents

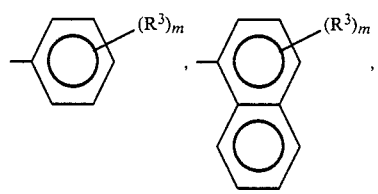

a 9-anthryl group or a substituted or unsubstituted N-alkylcarbazolyl group, wherein R[3] represents hydrogen, an alkyl group, an alkoxy group, a halogen or a substituted amino group represented by

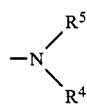

in which R[4] and R[5] independently represent an alkyl group, a substituted or unsubstituted aryl group, or a substituted or unsubstituted aralkyl group, and R[4] or R[5] may form a ring in combination, and m is an integer of 0 through 3, and n is an integer of 0 or 1, provided that, when R[1] is hydrogen and n=0, A is

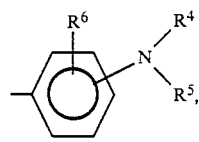

in which R[6] is hydrogen, an alkyl group, an alkoxy group or a halogen, and R[4] and R[5] are the same as defined previously.

DETAILED DESCRIPTION OF THE PREFERRED EMBODIMENTS

Figure 1:
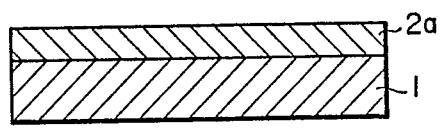
FIG. 1 is an enlarged schematic cross-sectional view of an embodiment of an electrophotographic photoconductor according to the present invention.

Referring to FIG. 1, there is shown an enlarged schematic cross-sectional view of an embodiment of an electrophotographic photoconductor according to the present invention. In the figure, reference numeral 1 indicates an electroconductive support material and reference numeral 2a represents a photosensitive layer which contains a novel stilbene derivative of the following general formula (I), a sensitizer dye and a binder agent.

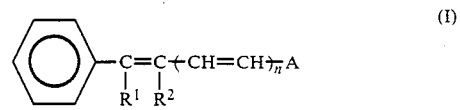

wherein R[1] represents hydrogen or

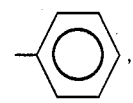

R[2] represents hydrogen, an alkyl group or a substituted or unsubstituted phenyl group; A represents

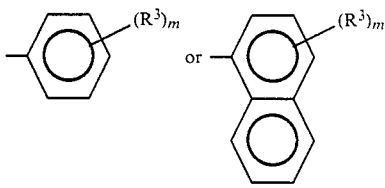

when R[1] is hydrogen; while, when R[1] is

A represents

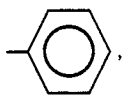

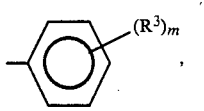

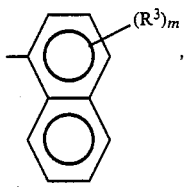

a 9-anthryl group or a substituted or unsubstituted N-alkylcarbazolyl group, wherein $R^3$ represents hydrogen, an alkyl group, an alkoxy group, a halogen or a substituted amino group represented by

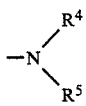

in which $R^4$ and $R^5$ independently represent an alkyl group, a substituted or unsubstituted aryl group, or a substituted or unsubstituted aralkyl group, and $R^4$ and $R^5$ may form a ring in combination (when $R^4$ and $R^5$ are a substituted aryl group and a substituted aralkyl group, the substituents are, for example, an alkyl group, an alkoxy group, a thioalkoxy group, a phenoxy group, halogen, a dialkylamino group, a hydroxyl group, a carboxy group and esters thereof, an acyl group, an aryloxy group, an aralkyloxy group, a trifluoromethyl group, a nitro group and a cyano group), m is an integer of 0 through 3 and n is an integer of 0 or 1, provided that, when $R^1$ is hydrogen and n=0, A is

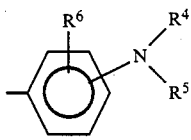

in which $R^6$ is hydrogen, an alkyl group, an alkoxy group or a halogen, and $R^4$ and $R^5$ are the same as defined previously.

The stilbene compound contained in the photosensitive layer 2a works as a photoconductive material. However, the stilbene compound itself scarcely absorbs light in the visible light range and, therefore, it is necessary to add a sensitizer dye which absorbs light in the visible light range in order to form latent electrostatic images by use of visible light.

In general, the above stilbene compounds can be used as a photoconductive material in combination with the above-mentioned sensitizer dye. Further, these stilbene compounds can also be used as charge transporting materials in combination with conventional charge generating materials.

Figure 2:
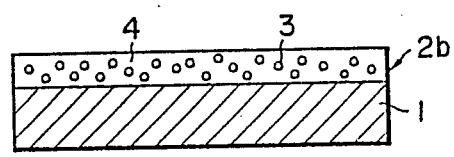
FIG. 2 is an enlarged schematic cross-sectional view of another embodiment of an electrophotographic photoconductor according to the present invention.

Referring to FIG. 2, there is shown an enlarged cross-sectional view of another embodiment of an electrophotographic photoconductor according to the present invention. In the figure, reference numeral 1 indicates an electroconductive support material. On the electroconductive support material 1, there is formed a photosensitive layer 2b comprising a charge generating material 3 dispersed in a charge transporting medium 4 comprising a stilbene compound and a binder agent. In this embodiment, the stilbene compound works as a charge transporting material; and the stilbene compound and the binder agent in combination constitute the charge transporting medium 4. To the charge transporting medium 4, in addition to the binder agent, a plasticizer can also be added. The charge generating material 3, which is, for example, an inorganic or organic pigment, generates charge carriers. The charge transporting medium 4 serves to accept the charge carriers generated by the charge generating material 3 and to transport those charge carriers.

In this electrophotographic photoconductor, it is basically necessary that the light-absorption wavelength regions of the charge generating material 3 and the stilbene compound not overlap in the visible light range. This is because, in order that the charge generating material 3 produce charge carriers efficiently, it is necessary that light pass through the charge transporting medium 4 and reach the surface of the charge generating material 3. Since the stilbene compounds of the general formula I do not substantially absorb light in the visible range, they can work effectively as charge transporting materials in combination with the charge generating material 3 which absorbs the light in the visible region and generates charge carriers.

Figure 3:
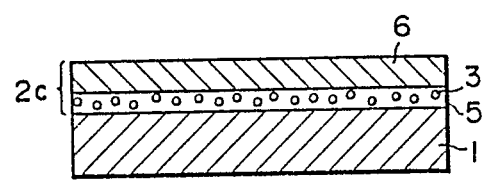
FIG. 3 is an enlarged schematic cross-sectional view of a further embodiment of an electrophotographic photoconductor according to the present invention.

Referring to FIG. 3, there is shown an enlarged cross-sectional view of a further embodiment of an electrophotographic photoconductor according to the present invention. In the figure, there is formed on the electroconductive support material 1 a two-layered photosensitive layer 2c comprising a charge generating layer 5 consisting essentially of the charge generating material 3, and a charge transporting layer 6 containing a stilbene compound of the previously described formula I.

In this photoconductor, light which has passed through the charge transporting layer 6 reaches the charge generating layer 5, and charge carriers are generated within the charge generating layer 5. The charge carriers which are necessary for the light decay for latent electrostatic image formation are generated by the charge generating material 3 and are accepted and transported by the charge transporting layer 6. In the charge transporting layer 6, the stilbene compound mainly works for transporting charge carriers. The generation and transportation of the charge carriers are performed by the same mechanism as that in the photoconductor shown in FIG. 2.

Preparation of representative stilbene compounds of the following formula Ia for use in the present invention will now be explained in detail:

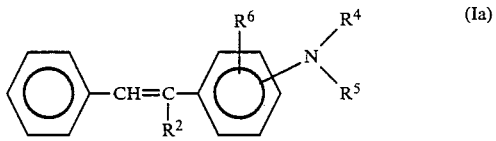

The above formula corresponds to the previously described formula I in the case where $R^1$ is hydrogen, n=0 and A is

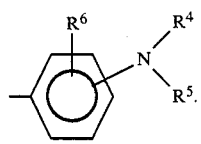

$R^2$, $R^4$, $R^5$ and $R^6$ are respectively the same as those defined in the general formula I.

Stilbene compounds of the above formula can be prepared by reacting a phenyl derivative of formula Ia-1 with a carbonyl compound of formula Ia-2 in the presence of a basic catalyst at temperatures ranging from room temperature to about 100° C.:

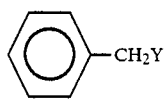

wherein Y represents a triphenylphosphonium group of the formula

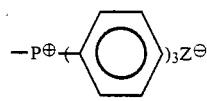

in which $Z^{\ominus}$ indicates a halogen ion; or a dialkoxyphosphorous group of formula —PO(OR)$_2$ in which R indicates a lower alkyl group;

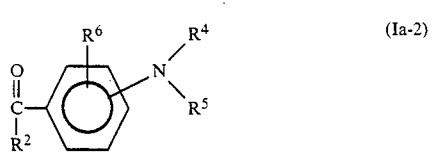

wherein $R^2$ represents hydrogen, an alkyl group or a substituted or unsubstituted phenyl group; $R^4$ and $R^5$ are the same as defined in the general formula I; and $R^6$ represents hydrogen, an alkyl group, an alkoxy group or a halogen.

The phenyl derivative of the formula Ia-1 can be prepared without difficulty by heating a corresponding halomethyl compound and a trialkyl phosphite or triphenylphosphine in a solvent, such as toluene, tetrahydrofuran or N,N-dimethylformamide.

As the trialkyl phosphite, those having alkyl groups with 1 to 4 carbon atoms, in particular, those having methyl groups or ethyl groups are preferable.

In the reaction of the phenyl derivative of the formula Ia-1 with the carbonyl compound of the formula Ia-2, as the basic catalyst, the following can be employed: sodium hydroxide, potassium hydroxide, sodium amide, sodium hydride; and alcoholates such as sodium methylate, and potassium-t-butoxide.

As the reaction solvent, the following can be employed: Methanol, ethanol, isopropanol, butanol, 2-methoxyethanol, 1,2-dimethoxyethane, bis(2-methoxyethyl) ether, dioxane, tetrahydrofuran, toluene, xylene, dimethyl sulfoxide, N,N-dimethylformamide, N-methylpyrrolidone and 1,3-dimethyl-2-imidazolidinone.

Of the above solvents, polar solvents, for example, N,N-dimethylformamide and dimethyl sulfoxide are particularly suitable for this reaction.

The reaction temperature for the above reaction can be set in a relatively wide range, depending upon (i) the stability of the solvent employed with the basic catalyst, (ii) the reactivities of the phenyl derivative of the formula Ia-1 and the carbonyl compound of the formula Ia-2, and (iii) the properties of the basic catalyst which works as a condensation agent in this reaction. When, for example, a polar solvent is employed as the reaction solvent, the reaction temperature can be set in the range of room temperature to about 100° C., more preferably in the range of room temperature to about 80° C. However, when the catalyst is not very reactive as the condensation agent, the reaction temperature can be raised beyond the aforementioned range.

Preparation of the stilbene compound of the formula Ia will now be explained in detail by referring to the following examples:

EXAMPLE 1

6.85 g (0.030 mol) of diethylbenzylphosphonate and 8.20 g (0.030 mol) of 4-N,N-diphenylaminobenzaldehyde were added to 40 ml of N,N-dimethylformamide. To this mixture, 8.70 g of a 28% methanol solution of sodium methylate was added dropwise over a period of 10 minutes. After the addition of the methanol solution of sodium methylate, the reaction mixture was stirred at temperatures ranging from 48° C. to 50° C. for 4 hours and was then cooled to room temperature. The reaction mixture was diluted with 30 ml of methanol and then with 10 ml of water. Crystals were separated from the reaction mixture, which were separated by filteration, washed with water and dried. The yield was 9.55 g (91.7%). The melting point of the thus obtained crystals was 151.5°–152.5° C.

Upon recrystallization of the crystals from ethyl acetate, 4-N,N-diphenylaminostilbene precipitated as light yellow needle-like crystals, corresponding to the stilbene compound No. 61 in Table 3. The melting point of the thus obtained 4-N,N-diphenylaminostilbene was at 152.0°–153.0° C.

The results of the elemental analysis of the thus obtained 4-N,N-diphenylaminostilbene were as follows:

|  | % C | % H | % N |
|---|---|---|---|
| Found | 89.84 | 6.01 | 4.00 |
| Calculated | 89.86 | 6.10 | 4.03 |

The above calculated amount were based on the formula for 4-N,N-diphenylaminostilbene of $C_{26}H_{21}N$.

Figure 4:
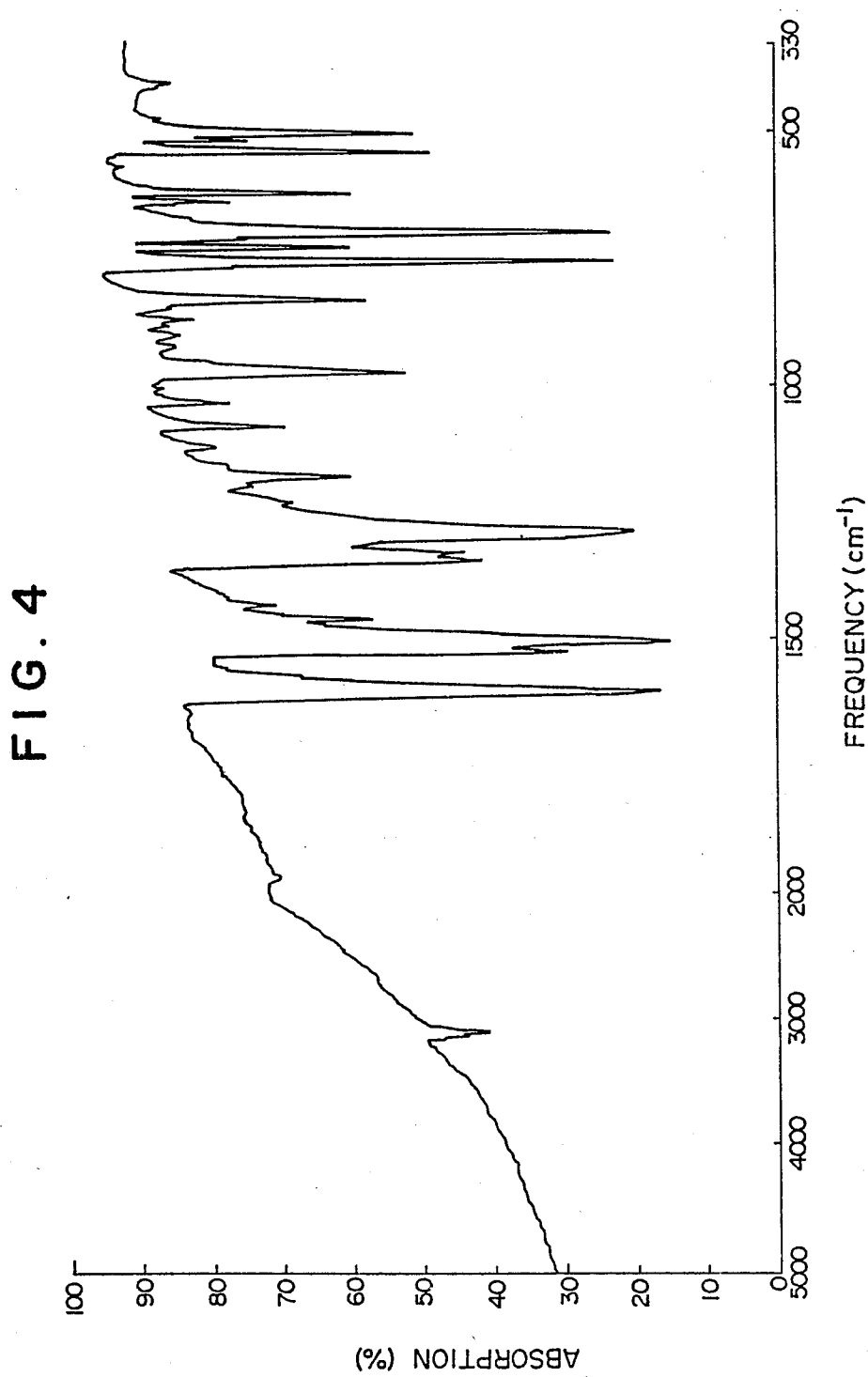
FIG. 4 is an infrared spectrum of stilbene compound No. 61 in Table 3.

An infrared spectrum of the 4-N,N-diphenylaminostilbene, taken by use of a KBr pellet, indicated a peak at 965 cm$^{-1}$ which is characteristic of the out-of-plane=CH (trans) deformation vibrations as shown in FIG. 4.

EXAMPLES 2 THROUGH 18

Example 1 was repeated except that 4-N,N-diphenylaminobenzaldehyde employed in Example 1 was replaced by the respective aldehydes listed in Table 1, whereby the novel stilbene compounds listed in Table 1 were obtained.

TABLE 1

| Example No. | Aldehyde | Product | Stilbene Compound No. in Table 3 |
|---|---|---|---|
| 2 | OHC–C₆H₄–N(CH₂–C₆H₅)₂ | C₆H₅–CH=CH–C₆H₄–N(CH₂–C₆H₅)₂ | 1 |
| 3 | OHC–C₆H₃(OCH₃)–N(CH₂–C₆H₅)₂ | C₆H₅–CH=CH–C₆H₃(OCH₃)–N(CH₂–C₆H₅)₂ | 8 |
| 4 | OHC–C₆H₃(CH₃)–N(CH₂–C₆H₅)₂ | C₆H₅–CH=CH–C₆H₃(CH₃)–N(CH₂–C₆H₅)₂ | 2 |
| 5 | OHC–C₆H₃(Cl)–N(CH₂–C₆H₅)₂ | C₆H₅–CH=CH–C₆H₃(Cl)–N(CH₂–C₆H₅)₂ | 6 |
| 6 | OHC–C₆H₄–N(CH₂–C₆H₄–CH₃)₂ | C₆H₅–CH=CH–C₆H₄–N(CH₂–C₆H₄–CH₃)₂ | 12 |
| 7 | OHC–C₆H₄–N(CH₂–C₆H₄–Cl)₂ | C₆H₅–CH=CH–C₆H₄–N(CH₂–C₆H₄–Cl)₂ | 18 |
| 8 | OHC–C₆H₄–N(CH₂–C₆H₄(Cl))₂ (ortho-Cl) | C₆H₅–CH=CH–C₆H₄–N(CH₂–C₆H₄(Cl))₂ | 20 |
| 9 | OHC–C₆H₄–N(C₆H₄–OCH₃)₂ | C₆H₅–CH=CH–C₆H₄–N(C₆H₄–OCH₃)₂ | 86 |
| 10 | OHC–C₆H₄–N(C₆H₄–CH₃)₂ | C₆H₅–CH=CH–C₆H₄–N(C₆H₄–CH₃)₂ | 62 |

TABLE 1-continued

| Example No. | Aldehyde | Product | Stilbene Compound No. in Table 3 |
|---|---|---|---|
| 11 | 4-(N-ethyl-N-phenylamino)benzaldehyde | corresponding stilbene | 121 |
| 12 | 4-(N-methyl-N-phenylamino)benzaldehyde | corresponding stilbene | 111 |
| 13 | 4-(N-benzyl-N-phenylamino)benzaldehyde | corresponding stilbene | 141 |
| 14 | 4-(N-(4-methylphenyl)-N-phenylamino)benzaldehyde | corresponding stilbene | 68 |
| 15 | 4-(N-(4-chlorophenyl)-N-phenylamino)benzaldehyde | corresponding stilbene | 100 |
| 16 | 4-(N-(4-methoxyphenyl)-N-phenylamino)benzaldehyde | corresponding stilbene | 88 |

TABLE 1-continued

| Example No. | Aldehyde | Product | Stilbene Compound No. in Table 3 |
|---|---|---|---|
| 17 | OHC-C6H4-N(C6H5)(C6H4-CN) | C6H5-CH=CH-C6H4-N(C6H5)(C6H4-CN) | 160 |
| 18 | OHC-C6H4-N(C6H5)(2,5-(CH3)2-C6H3) | C6H5-CH=CH-C6H4-N(C6H5)(2,5-(CH3)2-C6H3) | 161 |

The recrystallization solvents, melting points and the results of the elemental analyses of the above stilbene compounds prepared in Examples 2 through 18 were as follows:

TABLE 2

| Example No. | Recrystallization Solvent | Melting Point | Elemental Analysis Found/Calculated | | |
|---|---|---|---|---|---|
| | | | % C | % H | % N |
| 2 | Ethyl acetate - Ethanol | 146.5~147.5 | 89.81/ 89.55 | 6.65/ 6.72 | 3.69/ 3.73 |
| 3 | Ethyl acetate - Ethanol | 139.5~140.5 | 85.79/ 85.88 | 6.55/ 6.72 | 3.46/ 3.45 |
| 4 | Dioxane - Ethanol | 153.0~155.5 | 89.40/ 89.40 | 7.10/ 7.00 | 3.49/ 3.60 |
| 5 | Ethyl acetate | 172.0~173.0 | 82.26/ 82.01 | 5.74/ 5.91 | 3.40/ 3.42 |
| 6 | Ethyl acetate - Ethanol | 124.5~125.5 | 89.30/ 89.27 | 7.34/ 7.26 | 3.45/ 3.47 |
| 7 | Toluene - Ethanol | 119.5~122.0 | 75.40/ 75.65 | 5.01/ 5.23 | 3.22/ 3.15 |
| 8 | Dioxane - Ethanol | 188.5~189.5 | 75.41/ 75.65 | 5.24/ 5.23 | 3.06/ 3.15 |
| 9 | Ethyl acetate - Ethanol | 122.0~123.0 | 82.39/ 82.51 | 6.21/ 6.20 | 3.39/ 3.44 |
| 10 | Dioxane - Ethanol | 172.0~173.0 | 89.47/ 89.55 | 6.71/ 6.72 | 3.69/ 3.73 |
| 11 | Ethyl acetate - Ethanol | 111.5~112.0 | 88.30/ 88.24 | 6.91/ 7.08 | 4.58/ 4.68 |
| 12 | Dioxane - Ethanol | 129.5~130.5 | 88.41/ 88.37 | 6.69/ 6.72 | 4.87/ 4.91 |
| 13 | Ethyl acetate - Ethanol | 118.5~119.5 | 89.63/ 89.70 | 6.33/ 6.43 | 3.89/ 3.88 |
| 14 | Ethyl acetate - Ethanol | 136.5~137.5 | 89.58/ 89.70 | 6.36/ 6.43 | 3.86/ 3.88 |
| 15 | n-hexane-Cyclohexane | 110.5~111.5 | 81.83/ 81.76 | 5.24/ 5.29 | 3.60/ 3.67 |
| 16 | Ethyl acetate - Ethanol | 110.0~111.0 | 85.85/ 85.90 | 6.13/ 6.15 | 3.69/ 4.71 |
| 17 | Ethyl acetate - Ethanol | 127.5~128.5 | 87.05/ 87.05 | 5.37/ 5.42 | 7.54/ 7.52 |
| 18 | Ethyl acetate - Ethanol | 104.5~105.5 | 89.49/ 89.55 | 6.70/ 6.72 | 3.69/ 3.73 |

EXAMPLE 19

40 ml of tetrahydrofuran and 20 ml of 1,3-dimethyl-2-imidazolidinone were added to a mixture of 4.56 g (0.020 mol) of diethylbenzylphosphonate and 5.36 g (0.020 mol) of 4,4′-tetramethyl diaminobenzophenone. To this mixture, 1.44 g of a 50% sodium hydride was added and the mixture was refluxed for 20 hours. The mixture was then cooled to room temperature and water was added to the reaction mixture. Crystals were separated from the reaction mixture, which crystals were separated by filtration, washed with water and dried, whereby 6.3 g of light yellow powder was obtained. The thus obtained light yellow powder was added to 50 ml of toluene and dissolved therein. Insoluble components were filtered off and the filtrate was evaporated to dryness so that a solid material was obtained. The solid material was recrystallized from a mixed solvent of cyclohexane and ethanol, whereby α-(4-N,N-dimethylaminophenyl)-4-N,N-dimethylaminostilbene, corresponding to the stilbene compound No. 154 in Table 3, was obtained as yellow prism-like crystals. The yield was 1.4 g (20.4%). The melting point was at 131.5°–132.5° C.

The results of the elemental analysis of the thus obtained α-(4-N,N-dimethylaminophenyl)-4-N,N-dimethylaminostilbene) were as follows:

| | % C | % H | % N |
|---|---|---|---|
| Found | 83.88 | 7.67 | 8.05 |
| Calculated | 84.15 | 7.67 | 8.18 |

The above calculated amounts were based on the formula for α-(4-N,N-dimethylaminophenyl)-4-N,N-dimethylaminostilbene of $C_{24}H_{26}N$.

Figure 5:
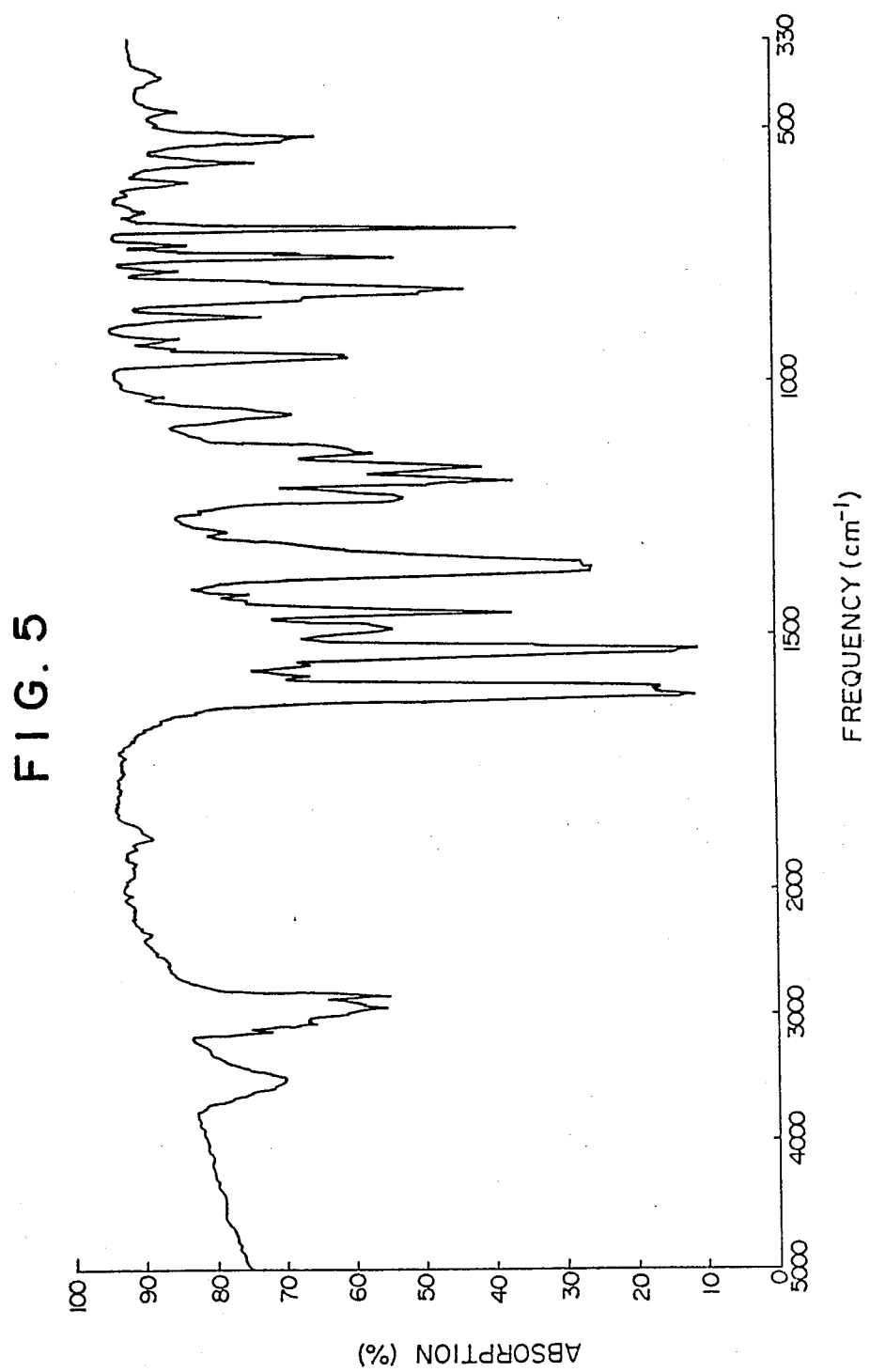
FIG. 5 is an infrared spectrum of stilbene compound No. 154 in Table 3.

An infrared spectrum of the α-(4-N,N-dimethylaminophenyl)-4-N,N-dimethylaminostilbene, which was taken by use of a KBr pellet, is shown in FIG. 5.

EXAMPLE 20

To a mixture of 3.89 g (0.01 mol) of benzyltriphenylphosphonium chloride and 2.74 g (0.01 mol) of 4-N,N-diphenylaminobenzylaldehyde, there was added 20 ml of N,N-dimethylformamide. To this mixture, 2.90 g of a 28% methanol solution of sodium methylate was added dropwise at temperatures ranging from 21° C. to 29° C. over a period of 25 minutes. After the dropwise addition of the methanol solution of sodium methylate, the reaction mixture was stirred at room temperature for 3 hours. The reaction mixture was then diluted with 30 ml of water. The product was extracted with toluene. The organic layer portion was washed with water and was then dried. The toluene was removed by evaporation from the organic layer portion, whereby light yellow crystals were obtained. The thus obtained light yellow crystals were recrystallized from cyclohexane in the presence of a small amount of iodine, whereby 2.60 g (74.9%) of 4-N,N-diphenylaminostilbene was obtained as light yellow needle-like crystals. The melting point of the product was at 152.0°–153.0° C.

The result of the elemental analysis of the thus obtained 4-N,N-diphenylaminostilbene were as follows:

|  | % C | % H | % N |
|---|---|---|---|
| Found | 89.79 | 6.08 | 4.02 |
| Calculated | 89.86 | 6.10 | 4.03 |

The above calculation was based on the formula for 4-N,N-diphenylaminostilbene of $C_{26}H_{21}N$.

An infrared spectrum of the 4-N,N-diphenylaminostilbene taken by use of a KBr pellet was exactly the same as that shown in FIG. 4.

In addition to the above-described stilbene compounds in Examples 1 through 20, other stilbene compounds of the formula Ia, that is,

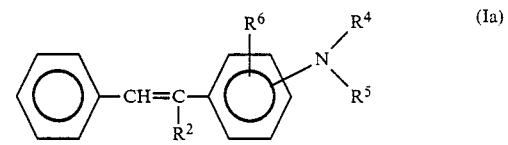

which are also particularly useful in the present invention, are listed in the following Table 3.

TABLE 3

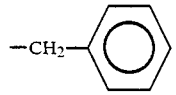

| Compound No. | $R^2$ | $R^6$ | | $R^4$ | $R^5$ |
|---|---|---|---|---|---|
| 1 | H | H | 4 | —CH₂—⌬ | —CH₂—⌬ |
| 2 | H | 2-CH₃ | 4 | —CH₂—⌬ | —CH₂—⌬ |
| 3 | H | 3-CH₃ | 4 | —CH₂—⌬ | —CH₂—⌬ |
| 4 | H | 2-C₂H₅ | 4 | —CH₂—⌬ | —CH₂—⌬ |
| 5 | H | 3-C₂H₅ | 4 | —CH₂—⌬ | —CH₂—⌬ |

TABLE 3-continued
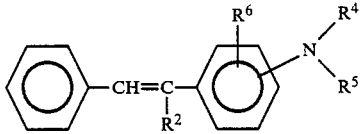
| Compound No. | R² | R⁶ | position | R⁴ | R⁵ |
|---|---|---|---|---|---|
| 6 | H | 2-Cl | 4 | −CH₂−C₆H₅ | −CH₂−C₆H₅ |
| 7 | H | 3-Cl | 4 | −CH₂−C₆H₅ | −CH₂−C₆H₅ |
| 8 | H | 2-OCH₃ | 4 | −CH₂−C₆H₅ | −CH₂−C₆H₅ |
| 9 | H | 3-OCH₃ | 4 | −CH₂−C₆H₅ | −CH₂−C₆H₅ |
| 10 | H | 2-OC₂H₅ | 4 | −CH₂−C₆H₅ | −CH₂−C₆H₅ |
| 11 | H | 3-OC₂H₅ | 4 | −CH₂−C₆H₅ | −CH₂−C₆H₅ |
| 12 | H | H | 4 | −CH₂−C₆H₄−CH₃ (4-) | −CH₂−C₆H₄−CH₃ (4-) |
| 13 | H | H | 4 | −CH₂−C₆H₄−CH₃ (3-) | −CH₂−C₆H₄−CH₃ (3-) |
| 14 | H | H | 4 | −CH₂−C₆H₄−CH₃ (2-) | −CH₂−C₆H₄−CH₃ (2-) |
| 15 | H | H | 4 | −CH₂−C₆H₄−C₂H₅ (4-) | −CH₂−C₆H₄−C₂H₅ (4-) |

TABLE 3-continued

[structure shown: Ph-CH=C(R²)-C₆H₃(R⁶)-N(R⁴)(R⁵)]

[structure shown: numbered aniline ring with positions 2,3,4 and N(R⁴)(R⁵)]

| Compound No. | R² | R⁶ | | R⁴ | R⁵ |
|---|---|---|---|---|---|
| 16 | H | H | 4 | —CH₂—C₆H₄(o-C₂H₅) | —CH₂—C₆H₄(o-C₂H₅) |
| 17 | H | H | 4 | —CH₂—C₆H₄(m-C₂H₅) | —CH₂—C₆H₄(m-C₂H₅) |
| 18 | H | H | 4 | —CH₂—C₆H₄(p-Cl) | —CH₂—C₆H₄(p-Cl) |
| 19 | H | H | 4 | —CH₂—C₆H₄(m-Cl) | —CH₂—C₆H₄(m-Cl) |
| 20 | H | H | 4 | —CH₂—C₆H₄(o-Cl) | —CH₂—C₆H₄(o-Cl) |
| 21 | H | H | 2 | —CH₂—C₆H₅ | —CH₂—C₆H₅ |
| 22 | H | H | 3 | —CH₂—C₆H₅ | —CH₂—C₆H₅ |
| 23 | H | 2-CH₃ | 4 | —CH₂—C₆H₄(p-CH₃) | —CH₂—C₆H₄(p-CH₃) |
| 24 | H | 2-CH₃ | 4 | —CH₂—C₆H₄(o-CH₃) | —CH₂—C₆H₄(o-CH₃) |
| 25 | H | 2-CH₃ | 4 | —CH₂—C₆H₄(p-OCH₃) | —CH₂—C₆H₄(p-OCH₃) |

TABLE 3-continued

| Compound No. | R² | R⁶ | | R⁴ | R⁵ |
|---|---|---|---|---|---|
| 26 | H | 2-CH₃ | 4 | —CH₂—C₆H₄—OC₂H₅ | —CH₂—C₆H₄—OC₂H₅ |
| 27 | H | 2-CH₃ | 4 | —CH₂—C₆H₄—Cl | —CH₂—C₆H₄—Cl |
| 28 | H | 2-CH₃ | 4 | —CH₂—C₆H₄(2-Cl) | —CH₂—C₆H₄(2-Cl) |
| 29 | H | 2-OCH₃ | 4 | —CH₂—C₆H₄—CH₃ | —CH₂—C₆H₄—CH₃ |
| 30 | H | 2-OCH₃ | 4 | —CH₂—C₆H₄(2-CH₃) | —CH₂—C₆H₄(2-CH₃) |
| 31 | H | 2-OCH₃ | 4 | —CH₂—C₆H₄—C₂H₅ | —CH₂—C₆H₄—C₂H₅ |
| 32 | H | 2-Cl | 4 | —CH₂—C₆H₄—CH₃ | —CH₂—C₆H₄—CH₃ |
| 33 | H | 2-Cl | 4 | —CH₂—C₆H₄(2-OC₂H₅) | —CH₂—C₆H₄(2-OC₂H₅) |
| 34 | H | 3-CH₃ | 4 | —CH₂—C₆H₄—CH₃ | —CH₂—C₆H₄—CH₃ |
| 35 | H | 3-CH₃ | 4 | —CH₂—C₆H₄(2-CH₃) | —CH₂—C₆H₄(2-CH₃) |

TABLE 3-continued
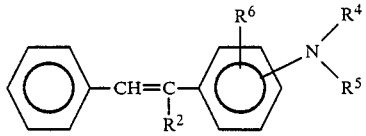
| Compound No. | R² | R⁶ | (position) | R⁴ | R⁵ |
|---|---|---|---|---|---|
| 36 | H | 3-CH₃ | 4 | —CH₂—C₆H₄—C₂H₅ | —CH₂—C₆H₄—C₂H₅ |
| 37 | H | 2-OC₂H₅ | 4 | —CH₂—C₆H₄—CH₃ | —CH₂—C₆H₄—CH₃ |
| 38 | H | 3-Cl | 4 | —CH₂—C₆H₄(CH₃) | —CH₂—C₆H₄(CH₃) |
| 39 | H | 3-Cl | 4 | —CH₂—C₆H₄—C₂H₅ | —CH₂—C₆H₄—C₂H₅ |
| 40 | H | H | 2 | —CH₂—C₆H₄—CH₃ | —CH₂—C₆H₄—CH₃ |
| 41 | H | H | 3 | —CH₂—C₆H₄—OCH₃ | —CH₂—C₆H₄—OCH₃ |
| 42 | H | H | 4 | —CH₃ | —CH₂—C₆H₅ |
| 43 | H | H | 4 | —C₂H₅ | —CH₂—C₆H₅ |
| 44 | H | H | 4 | —(CH₂)₂CH₃ | —CH₂—C₆H₄—OCH₃ |
| 45 | H | H | 4 | —(CH₂)₃CH₃ | —CH₂—C₆H₅ |
| 46 | H | H | 4 | —CH(CH₃)CH₃ | —CH₂—C₆H₅ |

TABLE 3-continued
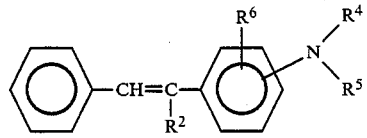
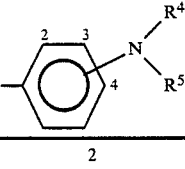
| Compound No. | R² | R⁶ | | R⁴ | R⁵ |
|---|---|---|---|---|---|
| 47 | H | H | 2 | —CH₃ | —CH₂—C₆H₅ |
| 48 | H | H | 3 | —CH₃ | —CH₂—C₆H₅ |
| 49 | H | 2-CH₃ | 4 | —CH₃ | —CH₂—C₆H₅ |
| 50 | H | 2-C₂H₅ | 4 | —CH₃ | —CH₂—C₆H₅ |
| 51 | H | 2-Cl | 4 | —CH₃ | —CH₂—C₆H₅ |
| 52 | H | 2-C₂H₅ | 4 | —CH₃ | —CH₂—C₆H₅ |
| 53 | H | 2-OC₂H₅ | 4 | —CH₃ | —CH₂—C₆H₅ |
| 54 | H | 2-CH₃ | 4 | —CH₃ | —CH₂—C₆H₄—CH₃ |
| 55 | H | 2-CH₃ | 4 | —CH₃ | —CH₂—C₆H₄(CH₃) (ortho) |
| 56 | H | 2-CH₃ | 4 | —C₂H₅ | —CH₂—C₆H₄—CH₃ |
| 57 | H | 2-OCH₃ | 4 | —CH₃ | —CH₂—C₆H₄—OCH₃ |

TABLE 3-continued
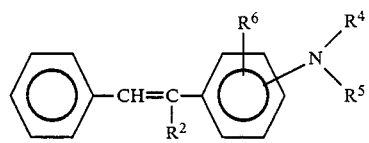
| Compound No. | R² | R⁶ | | R⁴ | R⁵ |
|---|---|---|---|---|---|
| 58 | H | 2-OCH₃ | 4 | —CH₃ | —CH₂—C₆H₄—CH₃ |
| 59 | H | H | 2 | —CH₃ | —CH₂—C₆H₅ |
| 60 | H | H | 3 | —CH₃ | —CH₂—C₆H₅ |
| 61 | H | H | 4 | —C₆H₅ | —C₆H₅ |
| 62 | H | H | 4 | —C₆H₄—CH₃ | —C₆H₄—CH₃ |
| 63 | H | H | 4 | —C₆H₄—C₂H₅ | —C₆H₄—C₂H₅ |
| 64 | H | H | 4 | —C₆H₄—(CH₂)₂CH₃ | —C₆H₄—(CH₂)₂CH₃ |
| 65 | H | H | 4 | —C₆H₄—CH(CH₃)CH₃ | —C₆H₄—CH(CH₃)CH₃ |
| 66 | H | H | 4 | —C₆H₄—(CH₂)₃CH₃ | —C₆H₄—(CH₂)₃CH₃ |
| 67 | H | H | 4 | —C₆H₄—C(CH₃)₃ | —C₆H₄—C(CH₃)₃ |
| 68 | H | H | 4 | —C₆H₅ | —C₆H₄—CH₃ |

TABLE 3-continued
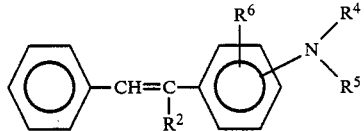
| Compound No. | R² | R⁶ | (position) | R⁴ | R⁵ |
|---|---|---|---|---|---|
| 69 | H | H | 4 | 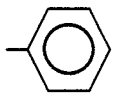 | 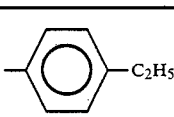 —C₂H₅ |
| 70 | H | H | 4 | 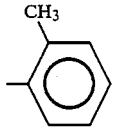 CH₃ | 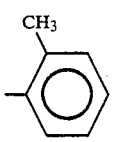 CH₃ |
| 71 | H | H | 4 | 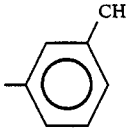 CH₃ | 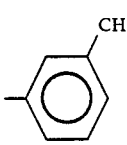 CH₃ |
| 72 | H | H | 4 | 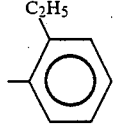 C₂H₅ | 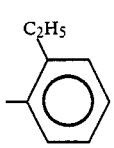 C₂H₅ |
| 73 | H | H | 4 | 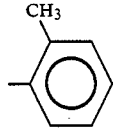 CH₃ | 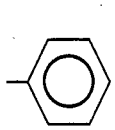 |
| 74 | H | H | 2 | 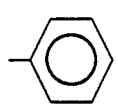 | 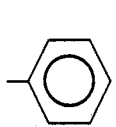 |
| 75 | H | H | 2 | 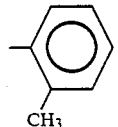 CH₃ | 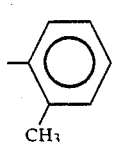 CH₃ |
| 76 | H | H | 2 | 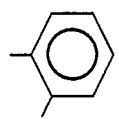 OCH₃ | 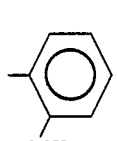 OCH₃ |
| 77 | H | H | 2 | 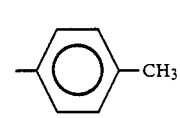 —CH₃ | 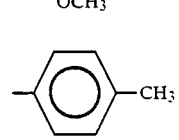 —CH₃ |
| 78 | H | H | 2 | 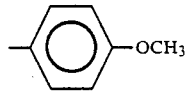 —OCH₃ | 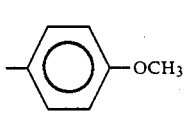 —OCH₃ |

TABLE 3-continued
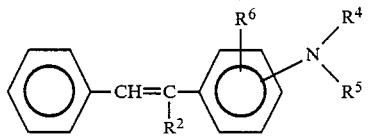
| Compound No. | R² | R⁶ | (position) | R⁴ | R⁵ |
|---|---|---|---|---|---|
| 79 | H | H | 2 | 3-methylphenyl | 3-methylphenyl |
| 80 | H | H | 2 | —CH₃ | phenyl |
| 81 | H | H | 2 | —C₂H₅ | phenyl |
| 82 | H | H | 2 | —CH₃ | 4-methoxyphenyl |
| 83 | H | H | 3 | phenyl | phenyl |
| 84 | H | H | 3 | 4-methylphenyl | 4-methylphenyl |
| 85 | H | H | 3 | 4-methoxyphenyl | 4-methoxyphenyl |
| 86 | H | H | 4 | 4-methoxyphenyl | 4-methoxyphenyl |
| 87 | H | H | 4 | 2-methoxyphenyl | 2-methoxyphenyl |
| 88 | H | H | 4 | 4-methoxyphenyl | phenyl |

TABLE 3-continued

| Compound No. | R² | R⁶ | (position) | R⁴ | R⁵ |
|---|---|---|---|---|---|
| 89 | H | H | 4 | 4-CH₃O-C₆H₄- | 3-CH₃O-C₆H₄- |
| 90 | H | H | 4 | 4-C₂H₅O-C₆H₄- | 4-C₂H₅O-C₆H₄- |
| 91 | H | H | 4 | 4-C₂H₅O-C₆H₄- | C₆H₅- |
| 92 | H | H | 4 | 4-CH₃O-C₆H₄- | 4-CH₃-C₆H₄- |
| 93 | H | H | 4 | 4-C₂H₅O-C₆H₄- | 4-CH₃-C₆H₄- |
| 94 | H | H | 4 | 4-CH₃O-C₆H₄- | 4-C₂H₅-C₆H₄- |
| 95 | H | H | 4 | 2-CH₃O-C₆H₄- | 4-CH₃-C₆H₄- |
| 96 | H | H | 4 | 4-Cl-C₆H₄- | 4-C₂H₅-C₆H₄- |
| 97 | H | H | 4 | 4-Cl-C₆H₄- | 4-Cl-C₆H₄- |
| 98 | H | H | 4 | 3-Cl-C₆H₄- | 3-Cl-C₆H₄- |

TABLE 3-continued
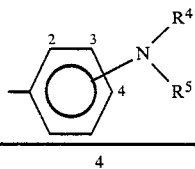
| Compound No. | R² | R⁶ | (position) | R⁴ | R⁵ |
|---|---|---|---|---|---|
| 99 | H | H | 4 |  3-Cl-C₆H₄ | 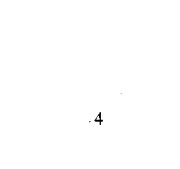 3-Cl-C₆H₄ |
| 100 | H | H | 4 |  4-Cl-C₆H₄ | 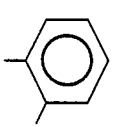 C₆H₅ |
| 101 | H | H | 4 | 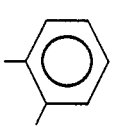 3-Cl-C₆H₄ | 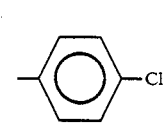 C₆H₅ |
| 102 | H | H | 4 | 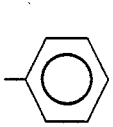 2-Cl-C₆H₄ | 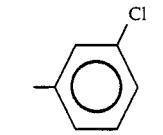 C₆H₅ |
| 103 | H | H | 4 | 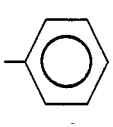 3-CH₃-C₆H₄ | 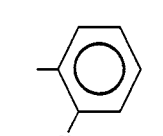 C₆H₅ |
| 104 | H | H | 4 | 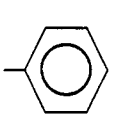 3-C₂H₅-C₆H₄ | 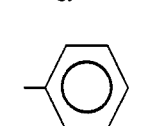 C₆H₅ |
| 105 | H | H | 4 | 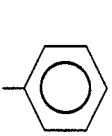 2-OCH₃-C₆H₄ | 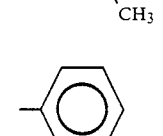 C₆H₅ |
| 106 | H | H | 4 | 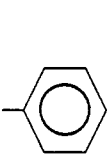 3-OCH₃-C₆H₄ | 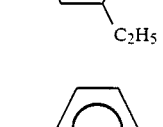 C₆H₅ |
| 107 | H | H | 4 |  4-N(CH₃)₂-C₆H₄ | 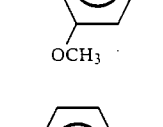 C₆H₅ |

TABLE 3-continued

| Compound No. | R² | R⁶ | position | R⁴ | R⁵ |
|---|---|---|---|---|---|
| 108 | H | H | 4 | 4-(C₂H₅)₂N-C₆H₄- | C₆H₅- |
| 109 | H | H | 4 | 4-(CH₃)₂N-C₆H₄- | 4-(CH₃)₂N-C₆H₄- |
| 110 | H | H | 4 | 4-(C₂H₅)₂N-C₆H₄- | 4-(C₂H₅)₂N-C₆H₄- |
| 111 | H | H | 4 | —CH₃ | C₆H₅- |
| 112 | H | H | 4 | —CH₃ | 4-CH₃-C₆H₄- |
| 113 | H | H | 4 | —CH₃ | 4-C₂H₅-C₆H₄- |
| 114 | H | H | 4 | —CH₃ | 2-CH₃-C₆H₄- |
| 115 | H | H | 4 | —CH₃ | 3-CH₃-C₆H₄- |
| 116 | H | H | 4 | —CH₃ | 4-OCH₃-C₆H₄- |
| 117 | H | H | 4 | —CH₃ | 4-OC₂H₅-C₆H₄- |

TABLE 3-continued
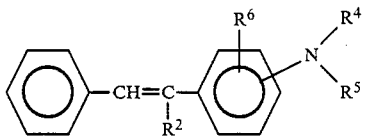
| Compound No. | $R^2$ | $R^6$ | (position) | $R^4$ | $R^5$ |
|---|---|---|---|---|---|
| 118 | H | H | 4 | $-CH_3$ | 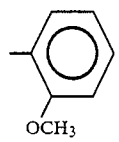 (2-OCH₃-phenyl) |
| 119 | H | H | 4 | $-CH_3$ | 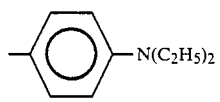 (4-N(C₂H₅)₂-phenyl) |
| 120 | H | H | 4 | $-CH_3$ | 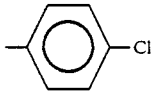 (4-Cl-phenyl) |
| 121 | H | H | 4 | $-C_2H_5$ | 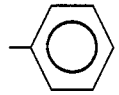 (phenyl) |
| 122 | H | H | 4 | $-C_2H_5$ | 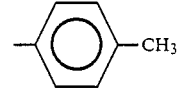 (4-CH₃-phenyl) |
| 123 | H | H | 4 | $-C_2H_5$ | 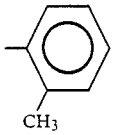 (3-CH₃-phenyl) |
| 124 | H | H | 4 | $-C_2H_5$ | 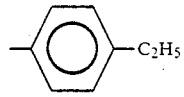 (4-C₂H₅-phenyl) |
| 125 | H | H | 4 | $-C_2H_5$ | 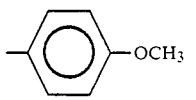 (4-OCH₃-phenyl) |
| 126 | H | H | 4 | $-C_2H_5$ | 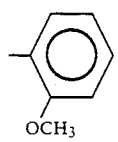 (2-OCH₃-phenyl) |
| 127 | H | H | 4 | $-C_2H_5$ | 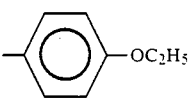 (4-OC₂H₅-phenyl) |

TABLE 3-continued
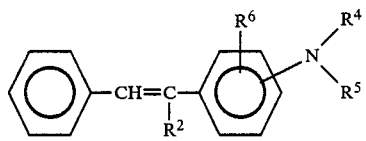
| Compound No. | R² | R⁶ | (position) | R⁴ | R⁵ |
|---|---|---|---|---|---|
| 128 | H | H | 4 | —C₂H₅ | 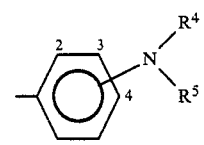 —N(CH₃)₂ |
| 129 | H | H | 4 | —C₂H₅ | 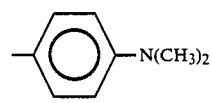 —Cl |
| 130 | H | H | 4 | —(CH₂)₂CH₃ | 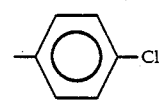 |
| 131 | H | H | 4 | —(CH₂)₂CH₃ | 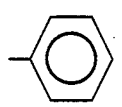 —CH₃ |
| 132 | H | H | 4 | —(CH₂)₂CH₃ | 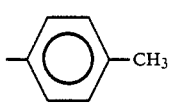 —OCH₃ |
| 133 | H | H | 4 | —(CH₂)₂CH₃ | 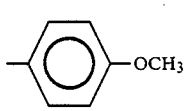 —Cl |
| 134 | H | H | 4 | —(CH₂)₂CH₃ | 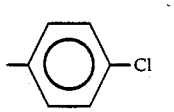 —N(CH₃)₂ |
| 135 | H | H | 4 | —(CH₂)₃CH₃ | 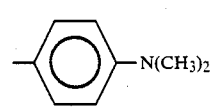 —CH₃ |
| 136 | H | H | 4 | —(CH₂)₃CH₃ | 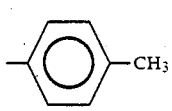 —OCH₃ |
| 137 | H | H | 4 | —(CH₂)₃CH₃ | 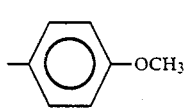 —Cl |
| 138 | H | H | 4 | —(CH₂)₃CH₃ | 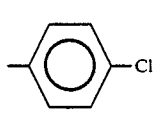 —N(CH₃)₂ |

TABLE 3-continued
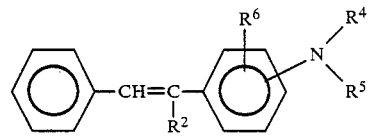
| Compound No. | R² | R⁶ | | R⁴ | R⁵ |
|---|---|---|---|---|---|
| 139 | H | H | 2 | —CH₃ | 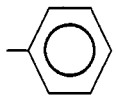 |
| 140 | H | H | 3 | —CH₃ | 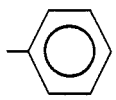 |
| 141 | H | H | 4 | —CH₂—⌬ | 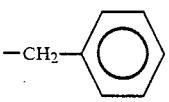 |
| 142 | H | H | 4 | —CH₂—⌬—CH₃ | 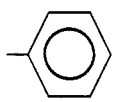 |
| 143 | H | H | 4 | —CH₂—⌬(CH₃) | 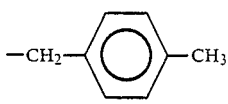 |
| 144 | H | H | 4 | —CH₂—⌬(CH₃) | 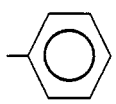 |
| 145 | H | H | 4 | —CH₂—⌬—OCH₃ | 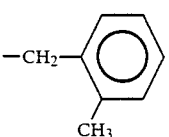 |
| 146 | H | H | 4 | —CH₂—⌬—OC₂H₅ | 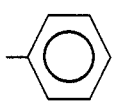 |
| 147 | H | H | 4 | —CH₂—⌬(OCH₃) | 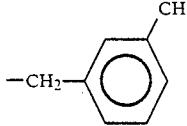 |
| 148 | H | H | 4 | —CH₂—⌬(OCH₃) | 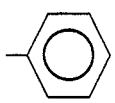 |

TABLE 3-continued

| Compound No. | R² | R⁶ | (position) | R⁴ | R⁵ |
|---|---|---|---|---|---|
| 149 | H | H | 4 | —CH₂—C₆H₄—Cl (4-Cl) | —C₆H₅ |
| 150 | H | H | 4 | —CH₂—C₆H₄—Cl (3-Cl) | —C₆H₅ |
| 151 | H | H | 4 | —CH₂—C₆H₄—Cl (2-Cl) | —C₆H₅ |
| 152 | H | H | 3 | —CH₂—C₆H₅ | —C₆H₅ |
| 153 | H | H | 2 | —CH₂—C₆H₅ | —C₆H₅ |
| 154 | —C₆H₄—N(CH₃)₂ | H | 4 | —CH₃ | —CH₃ |
| 155 | —C₆H₄—N(C₂H₅)₂ | H | 4 | —C₂H₅ | —C₂H₅ |
| 156 | — | H | 4 | —CH₃ | —CH₃ |
| 157 | — | H | 4 | —C₂H₅ | —C₂H₅ |
| 158 | H | H | 4 | —CH₂—C₆H₄—OCH₃ (4-OCH₃) | —CH₂—C₆H₄—OCH₃ (4-OCH₃) |
| 159 | H | H | 4 | —CH₂—C₆H₄—OCH₃ (2-OCH₃) | —CH₂—C₆H₄—OCH₃ (2-OCH₃) |
| 160 | H | H | 4 | —C₆H₅ | —C₆H₄—CN |

TABLE 3-continued

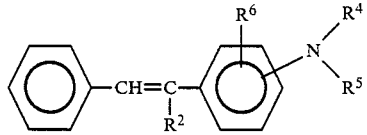

| Compound No. | $R^2$ | $R^6$ | (position on ring) | $R^4$ | $R^5$ |
|---|---|---|---|---|---|
| 161 | H | H | 4 | phenyl | 2,5-dimethylphenyl |

α-Phenylstilbene compounds of the following formula Ib can also be used in the present invention:

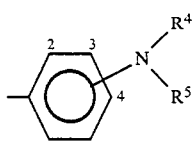 (Ib)

The above formula corresponds to the previously described formula I in the case where $R^1$ is

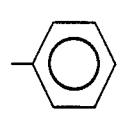;

and A and n are respectively the same as defined in the general formula I.

α-Phenylstilbene compounds of the above formula can be prepared by reacting a 1,1-diphenylmethyl derivative of formula Ib-1 with a carbonyl compound of formula Ib-2 in the presence of a basic catalyst at temperatures ranging from room temperature to about 100° C.

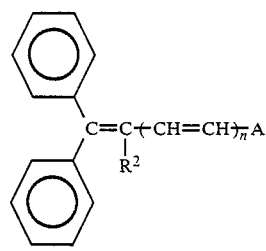 (Ib-1)

wherein Y represents a triphenylphosphonium group of the formula

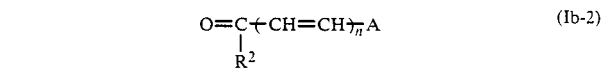

in which $Z^\ominus$ indicates a halogen ion; or a dialkoxyphosphorous group of the formula $-PO(OR)_2$ in which R indicates a lower alkyl group.

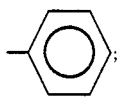 (Ib-2)

wherein n and A are the same as defined in the general formula I.

The 1,1-diphenylmethyl derivative of the formula Ib-1 can be prepared without difficulty by heating a corresponding halomethyl compound and a trialkyl phosphite or triphenyl phosphine in a solvent, such as toluene or xylene. As the trialkyl phosphite, those having alkyl groups with 1 to 4 carbon atoms, in particular, those having methyl groups or ethyl groups are preferable.

In the reaction of the 1,1-diphenylmethyl derivative of the formula Ib-1 with the carbonyl compound of the formula Ib-2, as the basic catalyst, the following can be employed: sodium hydroxide, potassium hydroxide, sodium amide, sodium hydride, and alcoholates such as sodium methylate, potassium-t-butoxide.

As the solvent for this reaction, the following can be employed as in the case of the stilbene compounds of the formula Ia: methanol, ethanol, isopropanol, butanol, 2-methoxyethanol, 1,2-dimethoxyethane, bis(2-methoxyethyl) ether, dioxane, tetrahydrofuran, toluene, xylene, dimethyl sulfoxide, N,N-dimethylformamide, N-methylpyrrolidone and 1,3-dimethyl-2-imidazolidinone.

Of the above solvents, polar solvents, for example, N,N-dimethylformamide and dimethyl sulfoxide are particularly suitable for this reaction.

The reaction temperature for the above reaction can be set in a comparatively wide range, depending upon (i) the stability of the solvent employed with the basic catalyst, (ii) the reactivities of the 1,1-diphenylmethyl derivative of the formula Ib-1 and of the aldehyde compound of the formula Ia-2, and (iii) the properties of the basic catalyst which works as a condensation agent in this reaction. For example, when a polar solvent is employed as the reaction solvent, the reaction temperature can be set in the range of room temperature to about 100° C., more preferably in the range of room temperature to about 80° C. However, when the catalyst is not very reactive, the reaction temperature can be elevated beyond the aforementioned range.

Preparation of the stilbene compound of the formula Ib will now be explained in detail by referring to the following examples:

EXAMPLE 21

3.04 g (0.010 mol) of diethyl 1,1-diphenylmethylphosphonate and 1.49 g (0.010 mol) of 4-N,N-dimethylaminobenzaldehyde were added to 20 ml of 1,2-dimethoxyethane. To this mixture, 0.50 g of a 50% sodium hydride was added. After the addition of the sodium hydride, the reaction mixture was stirred at room temperature for 3 hours, was then refluxed for 30 minutes, and was then cooled to room temperature. The reaction mixture was added to 200 ml of water. Precipitates separated from the reaction mixture, were filtered off, washed with water and dried. The yield was 2.0 g (66.7%).

By recrystallization of the precipitates from ethyl alcohol, pure α-phenyl-4'-N,N-dimethylaminostilbene, corresponding to stilbene compound No. 298 in Table 6, was obtained. The melting point of the thus obtained α-phenyl-4'-N,N-dimethylaminostilbene was at 125.0°–125.5° C.

The results of the elemental analysis were as follows:

|  | % C | % H | % N |
|---|---|---|---|
| Found | 88.01 | 7.07 | 4.76 |
| Calculated | 88.24 | 7.08 | 4.68 |

The above calculated amounts were based on the formula for α-phenyl-4'-N,N-dimethylaminostilbene of $C_{22}H_{21}N$.

Figure 6:
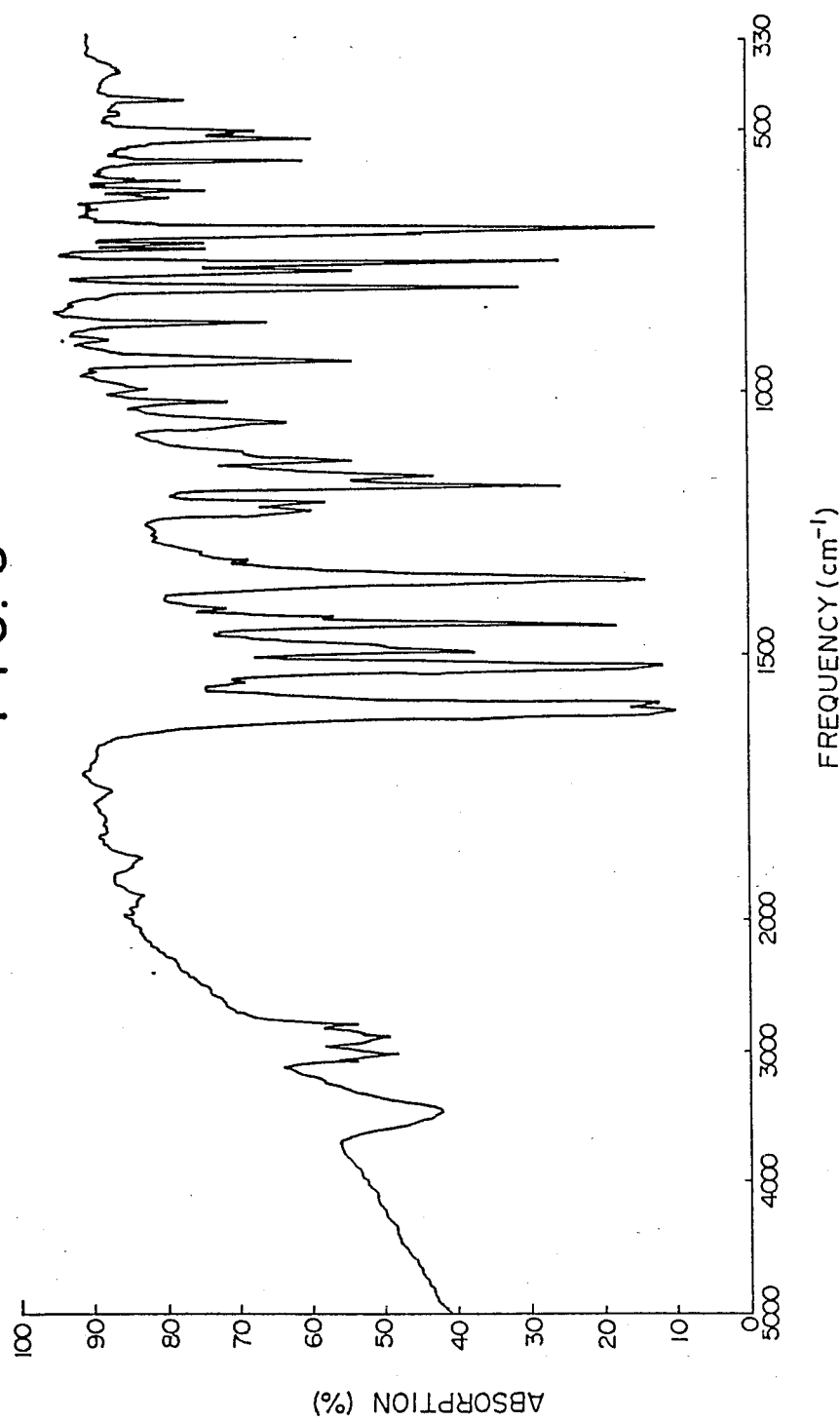
FIG. 6 is an infrared spectrum of stilbene compound No. 298 in Table 6.

An infrared spectrum of the product taken by use of a KBr pellet is shown in FIG. 6.

EXAMPLES 22 THROUGH 41

Example 21 was repeated except that 4-N,N-dimethylaminobenzaldehyde employed in Example 21 was replaced by the respective aldehydes listed in Table 4.

TABLE 4

| Example No. | Aldehyde | Product | Stilbene Compound No. in Table 6 |
|---|---|---|---|
| 22 | OHC—⟨C₆H₄⟩—N(C₂H₅)₂ | (C₆H₅)₂C=CH—⟨C₆H₄⟩—N(C₂H₅)₂ | 299 |
| 23 | OHC—⟨C₆H₃(Cl)⟩—N(CH₃)₂ | (C₆H₅)₂C=CH—⟨C₆H₃(Cl)⟩—N(CH₃)₂ | 190 |
| 24 | OHC—⟨C₆H₄⟩—N(CH₂—C₆H₅)₂ | (C₆H₅)₂C=CH—⟨C₆H₄⟩—N(CH₂—C₆H₅)₂ | 196 |

TABLE 4-continued

| Example No. | Aldehyde | Product | Stilbene Compound No. in Table 6 |
|---|---|---|---|
| 25 | 3-methyl-4-(dibenzylamino)benzaldehyde | corresponding stilbene | 197 |
| 26 | 3-methoxy-4-(dibenzylamino)benzaldehyde | corresponding stilbene | 202 |
| 27 | 3-chloro-4-(dibenzylamino)benzaldehyde | corresponding stilbene | 200 |
| 28 | 4-(diphenylamino)benzaldehyde | corresponding stilbene | 219 |
| 29 | anthracene-9-carbaldehyde | corresponding stilbene | 181 |
| 30 | 9-ethylcarbazole-3-carbaldehyde | corresponding stilbene | 182 |

TABLE 4-continued

| Example No. | Aldehyde | Product | Stilbene Compound No. in Table 6 |
|---|---|---|---|
| 31 | OHC—CH=CH—C₆H₄—N(CH₃)₂ | (C₆H₅)₂C=CH—CH=CH—C₆H₄—N(CH₃)₂ | 174 |
| 32 | OHC—CH=CH—C₆H₄(OCH₃) | (C₆H₅)₂C=CH—CH=CH—C₆H₄(OCH₃) | 300 |
| 33 | OHC—C₆H₃(OCH₃)(OCH₃) | (C₆H₅)₂C=CH—C₆H₃(OCH₃)(OCH₃) | 168 |
| 34 | OHC—C₆H₂(OCH₃)(OCH₃)(OCH₃) | (C₆H₅)₂C=CH—C₆H₂(OCH₃)(OCH₃)(OCH₃) | 169 |
| 35 | OHC—C₆H₄—N(C₆H₄—CH₃)₂ | (C₆H₅)₂C=CH—C₆H₄—N(C₆H₄—CH₃)₂ | 220 |
| 36 | OHC—C₆H₄—N(C₆H₄—OCH₃)₂ | (C₆H₅)₂C=CH—C₆H₄—N(C₆H₄—OCH₃)₂ | 235 |

TABLE 4-continued

| Example No. | Aldehyde | Product | Stilbene Compound No. in Table 6 |
|---|---|---|---|
| 37 | 4-OHC-C6H4-N(C6H5)(4-OCH3-C6H4) | Ph-C(=CH-C6H4-N(C6H5)(4-OCH3-C6H4))-Ph | 240 |
| 38 | 4-OHC-C6H4-N(C6H5)(4-CH3-C6H4) | Ph-C(=CH-C6H4-N(C6H5)(4-CH3-C6H4))-Ph | 226 |
| 39 | 4-OHC-C6H4-N(C6H5)(4-Cl-C6H4) | Ph-C(=CH-C6H4-N(C6H5)(4-Cl-C6H4))-Ph | 287 |
| 40 | 4-OHC-C6H4-N(C6H5)(4-CN-C6H4) | Ph-C(=CH-C6H4-N(C6H5)(4-CN-C6H4))-Ph | 288 |
| 41 | 4-OHC-C6H4-N(C6H5)(2,4-(CH3)2-C6H3) | Ph-C(=CH-C6H4-N(C6H5)(2,4-(CH3)2-C6H3))-Ph | 301 |

The recrystallization solvents, melting points and the results of the elemental analysis of the above stilbene compounds were as follows:

| | | | | | |
|---|---|---|---|---|---|
| 22 | Ethanol | 94.5~95.5 | 88.01/88.01 | 7.81/7.71 | 4.31/4.28 |
| 23 | Ethanol | 124.5~126.0 | 79.05/79.12 | 5.97/6.05 | 4.24/4.20 |
| 24 | Ligroin | 63.0~ | 90.34/90.41 | 6.28/6.49 | 3.03/3.10 |
| 25 | Ethyl Acetate | 169.0~170.7 | 90.01/90.27 | 6.64/6.72 | 3.03/3.01 |
| 26 | Ligroin | 125.80~126.0 | 87.49/87.27 | 6.55/6.50 | 2.74/2.91 |
| 27 | Toluene | 176.5~178.0 | 84.13/84.00 | 5.72/5.82 | 2.80/2.88 |
| 28 | Dioxane - Ethanol | 92.5~94/5 | 90.52/90.73 | 5.99/5.96 | 3.10/3.31 |
| 29 | Ethanol - Cyclohexane | 169.5~170.5 | 94.2/94.33 | 5.63/5.67 | — |
| 30 | Toluene - Ethanol | 139.5~140.5 | 90.12/90.03 | 6.17/6.22 | 3.64/3.75 |
| 31 | Dioxane - Methanol | 171.5~172.5 | 88.65/88.60 | 7.17/7.14 | 4.32/4.30 |
| 32 | Ethanol - Water | 104.5~105.5 | 88.38/88.41 | 6.32/6.47 | — |
| 33 | Ethanol - Water | 115.0~116.0 | 83.42/83.5 | 6.31/6.38 | — |
| 34 | Ethanol - Water | 98.0~99.0 | 79.75/79.73 | 6.33/6.41 | — |
| 35 | Dioxane - Methanol | 139.0~140.0 | 40.31/90.41 | 6.50/6.49 | 3.07/3.10 |
| 36 | Cyclohexane | 122.5~124.0 | 84.51/84.43 | 6.10/6.06 | 3.01/2.90 |
| 37 | Ethyl acetate - Ethanol | 125.5~126.5 | 87.29/87.37 | 5.98/6.01 | 3.01/3.09 |
| 38 | n-Hexane | 56 | 90.39/90.57 | 6.18/6.23 | 3.17/3.20 |
| 39 | — | (Oily material) | 83.99/83.91 | 5.31/5.29 | 3.01/3.06 |
| 40 | Ethyl acetate - Ethanol | 112.0~113.5 | 88.29/88.35 | 5.39/5.40 | 6.26/6.25 |
| 41 | (Washed with Methanol) | 60 | 90.29/90.41 | 6.29/6.40 | 3.02/3.10 |

Figure 7:
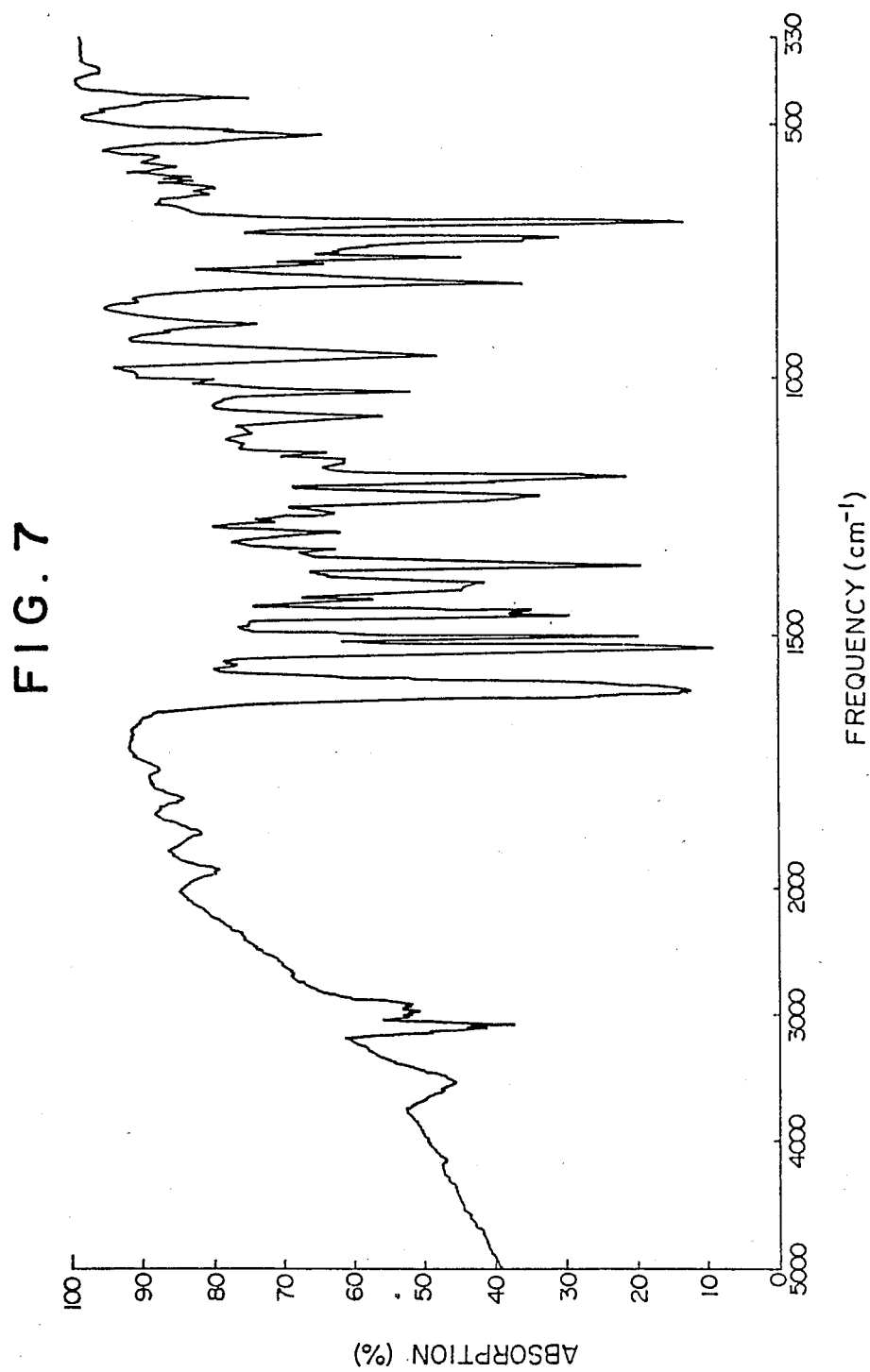
FIG. 7 is an infrared spectrum of stilbene compound No. 196 in Table 6.
Figure 8:
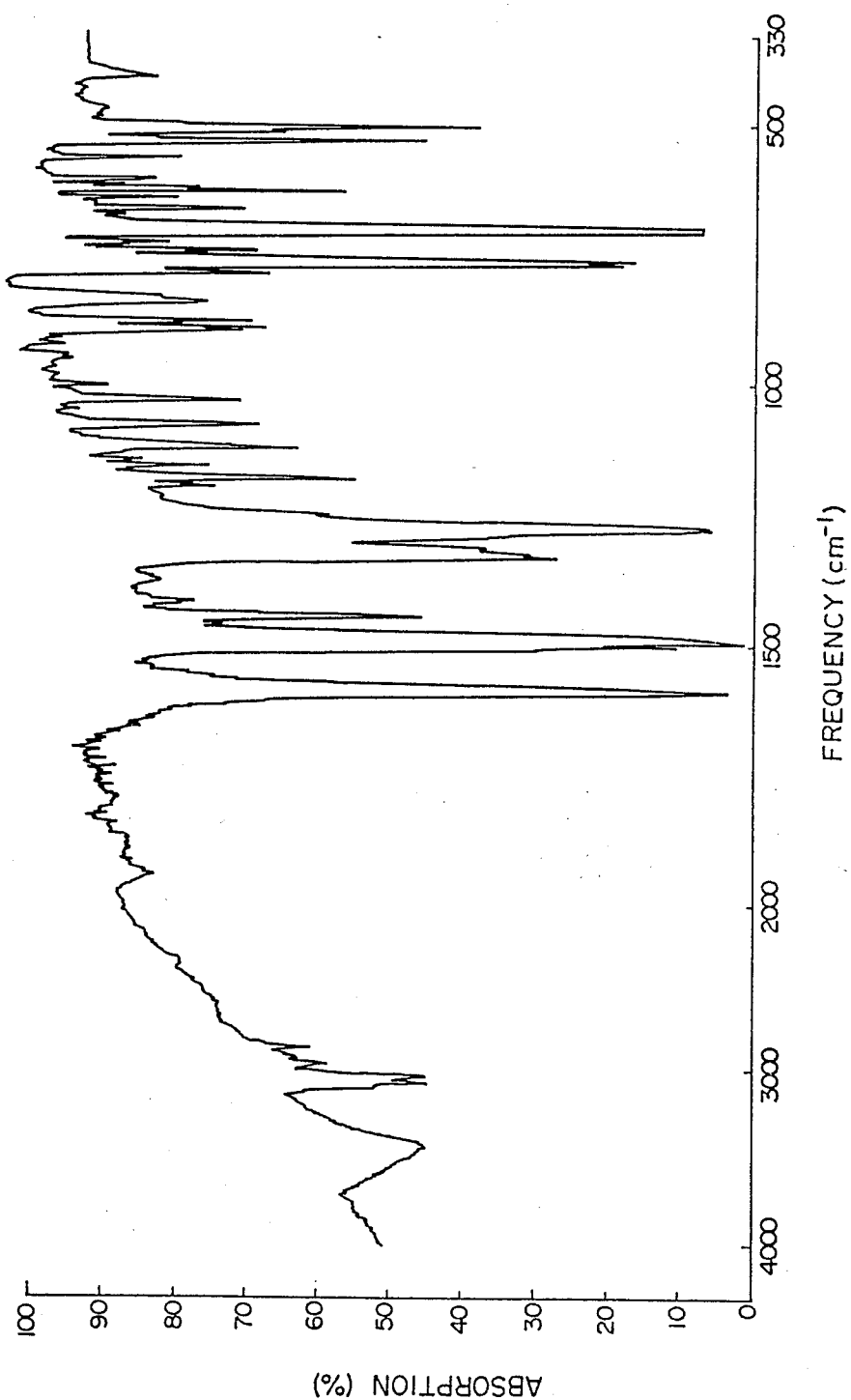
FIG. 8 is an infrared spectrum of stilbene compound No. 219 in Table 6.
Figure 9:
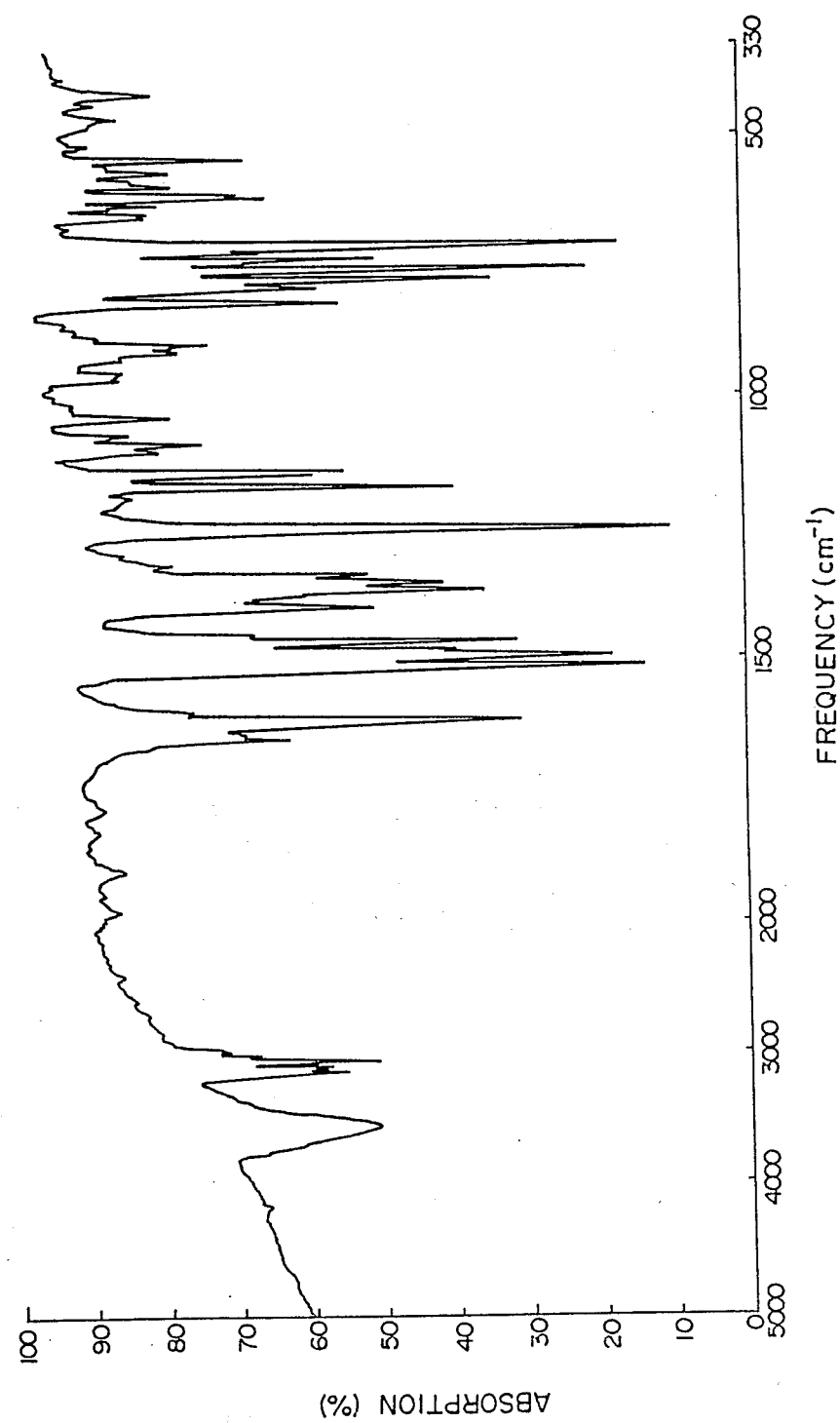
FIG. 9 is an infrared spectrum of stilbene compound No. 182 in Table 6.

The infrared spectra of α-phenyl-4'-N,N-dibenzylaminostilbene obtained in Example 24, α-phenyl-(4'-N,N-diphenylamino) stilbene obtained in Example 28, and 1,1-diphenyl-2-(3-N-ethylcarbazolyl) ethylene obtained in Example 30, taken by use of KBr pellets, are respectively shown in FIG. 7, FIG. 8 and FIG. 9.

EXAMPLE 42

6.50 g (0.021 mol) of diethyl 1,1-diphenylmethylphosphonate and 5.84 g (0.021 mol) of 4-N,N-diphenylaminobenzaldehyde were added to 40 ml of N,N-dimethylformaldehyde. To this mixture, 2.83 g (0.025 mol) of potassium-t-butoxide was gradually added at temperatures ranging from 21° C. to 33° C. over a period of 20 minutes. After the addition of the potassium-t-butoxide, the reaction mixture was stirred at room temperature for 4 hours and was then poured into 80 ml of ice water.

Precipitates, separated from the reaction mixture, were filtered off, washed with water and dried, whereby 8.20 g of a crude product was obtained in a 90.6% yield. The precipitates were recrystallized from a mixed solvent of toluene and ethanol light yellow needle-like crystals were filtered off. The thus obtained crystals were washed with methanol and dried, whereby pure α-phenyl-4'-N,N-diphenylaminostilbene with a melting point of 94.0° to 95.0° C. was obtained.

The results of the elemental analysis were as follows:

| | % C | % H | % N |
|---|---|---|---|
| Found | 90.68 | 5.91 | 3.32 |
| Calculated | 90.73 | 5.96 | 3.31 |

The above calculation was based on the formula for α-phenyl-4'-N,N-diphenylaminostilbene of $C_{32}H_{25}N$.

Figure 10:
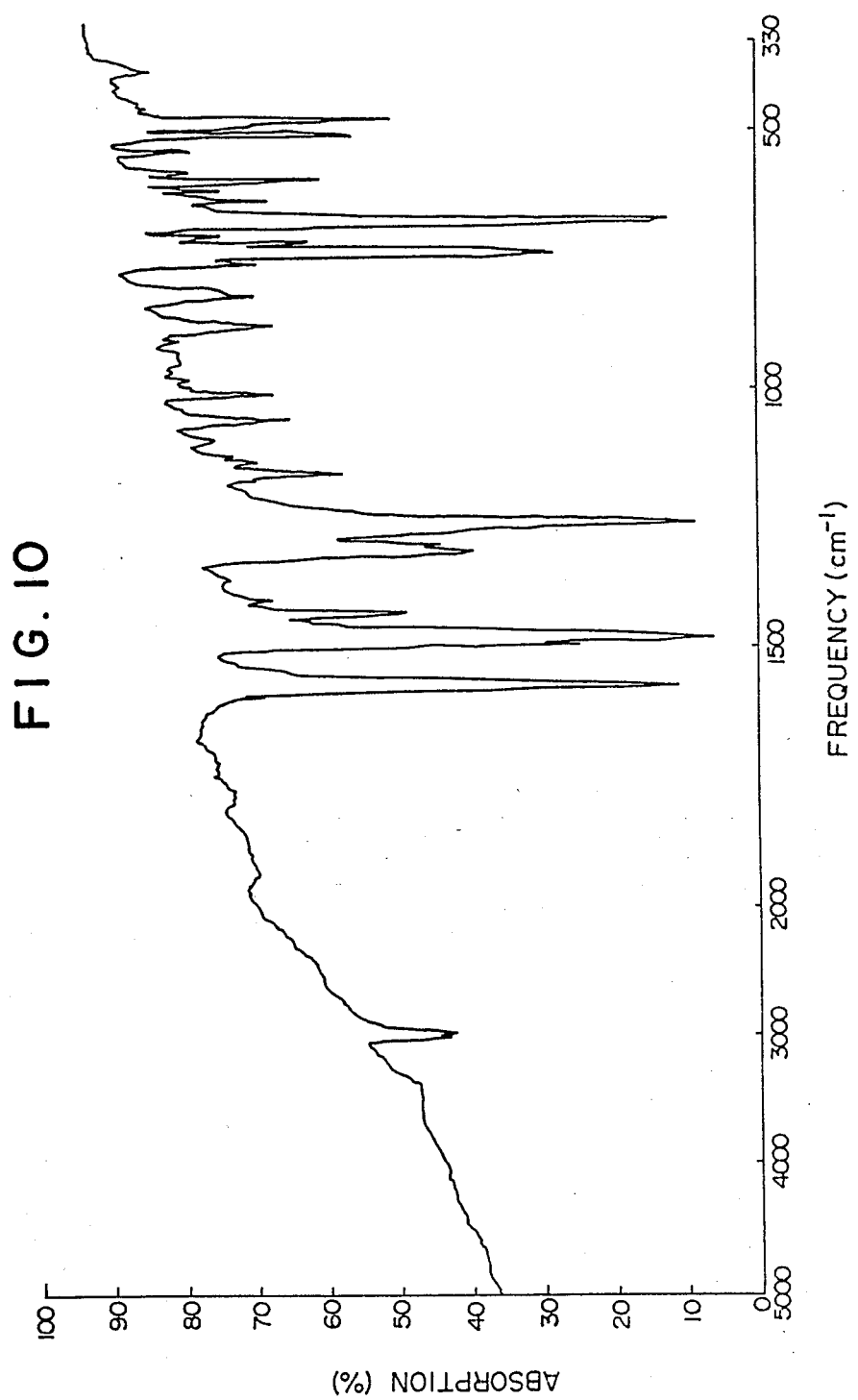
FIG. 10 is an infrared spectrum of stilbene compound No. 219 in Table 6, which was recrystallized by a solvent different from that employed for recrystallizing the stilbene compound No. 219 whose infrared spectrum is shown in FIG. 8.

An infrared spectrum of the stilbene compound taken by use of a KBr pellet is shown in FIG. 10.

EXAMPLE 43

5.09 g (0.010 mol) of 1,1-diphenylmethylphosphonium bromide and 2.74 g (0.010 mol) of 4-N,N-diphenylaminobenzaldehyde were added to 20 ml of N,N-dimethylformamide. To this mixture, 2.90 g of a 28% methanol solution of sodium methylate was added dropwise at temperatures ranging from 22° C. to 28° C., over a period of 30 minutes. After the addition of the sodium methylate, the reaction mixture was stirred at room temperature for 6 hours.

The reaction mixture was diluted with 50 ml of water. The reaction product was extracted by toluene from the reaction mixture. The organic layer was washed with water and dried. From the extraction liquid, toluene was eliminated by evaporation, and the residue was crystallized by addition of a small amount of ethanol. The crystals were filtered off, dried and recrystallized from a mixed solvent of n-hexane and toluene. The recrystallized crystals were washed with methanol and dried, so that 5.79 g of α-phenyl-4'-N,N-diphenylaminostilbene was obtained in the form of light yellow needle-like crystals in a 65% yield. The melting point of the α-phenyl-4'-N,N-diphenylaminostilbene was at 94.0°-95.0° C.

The results of the elemental analysis were as follows:

| | % C | % H | % N |
|---|---|---|---|
| Found | 90.48 | 5.91 | 3.19 |
| Calculated | 90.73 | 5.96 | 3.31 |

The above calculated amounts were based on the formula for α-phenyl-4'-N,N-diphenylaminostilbene of $C_{32}H_{25}N$.

An infrared spectrum of the stilbene compound taken by use of a KBr pellet was the same as that shown in FIG. 10.

In addition to the above described stilbene compounds in Examples 21 through 43, other stilbene compounds of the formula Ib, that is,

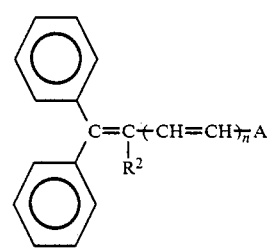

(Ib)

which are also particularly useful in the present invention, are listed in the following Table 6.

TABLE 6

$$\underset{\substack{\text{Ph} \\ \text{Ph}}}{\text{C}}=\underset{\substack{| \\ R^2}}{\text{C}}(\text{CH}=\text{CH})_n\text{A}$$

| Compound No. | n | R² | A |
|---|---|---|---|
| 162 | 0 | H | —C₆H₄—CH₃ (para) |
| 163 | 0 | H | —C₆H₃(CH₃)₂ (2,4-dimethyl) |
| 164 | 0 | H | —C₆H₄—C₂H₅ (para) |
| 165 | 0 | H | —C₆H₄—C(CH₃)₃ (para) |
| 166 | 0 | H | —C₆H₄—OC₂H₅ (ortho) |
| 167 | 0 | H | —C₆H₄—OCH₃ (para) |
| 168 | 0 | H | —C₆H₃(OCH₃)₂ (2,4-dimethoxy) |
| 169 | 0 | H | —C₆H₂(OCH₃)₃ (2,3,4-trimethoxy) |
| 170 | 0 | H | —C₆H₄—Cl (para) |

TABLE 6-continued
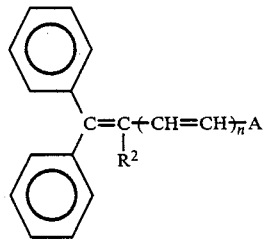
| Compound No. | n | R² | A |
|---|---|---|---|
| 171 | 0 | H | 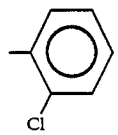 |
| 172 | 0 | H | 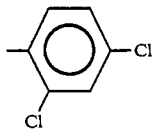 |
| 173 | 1 | H | 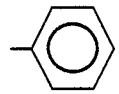 |
| 174 | 1 | H | 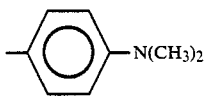 |
| 175 | 1 | H | 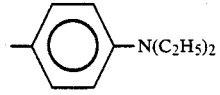 |
| 176 | 1 | H | 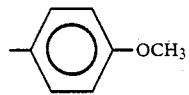 |
| 177 | 1 | H | 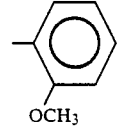 |
| 178 | 0 | H | 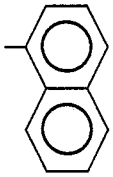 |

TABLE 6-continued $$\underset{R^2}{\overset{\phantom{R^2}}{\text{C}=\text{C}}}(\text{CH}=\text{CH})_n\text{A}$$
(with two phenyl groups on the left carbon)

| Compound No. | n | R² | A |
|---|---|---|---|
| 179 | 0 | H | 4-methyl-1-methoxynaphthyl |
| 180 | 0 | H | 3-methyl-2-methoxynaphthyl |
| 181 | 0 | H | anthryl |
| 182 | 0 | H | 9-ethyl-3-methylcarbazolyl |
| 183 | 0 | H | 9-ethyl-3-methyl-6-bromocarbazolyl |
| 184 | 0 | H | 9-methyl-3-methylcarbazolyl |
| 185 | 0 | H | 9-propyl-3-methylcarbazolyl |
| 186 | 0 | H | 9-butyl-3-methylcarbazolyl |

TABLE 6-continued (Ph)(Ph)C=C(R²)(CH=CH)ₙA

| Compound No. | n | R² | A |
|---|---|---|---|
| 187 | 0 | –C₆H₄– | –C₆H₅ |
| 188 | 0 | –C₆H₄–N(CH₃)₂ | –C₆H₄–N(CH₃)₂ |
| 189 | 0 | –C₆H₄–N(C₂H₅)₂ | –C₆H₄–N(C₂H₅)₂ |
| 190 | 0 | H | –C₆H₃(Cl)–N(CH₃)₂ |
| 191 | 0 | H | –C₆H₃(CH₃)–N(C₂H₅)₂ |
| 192 | 0 | H | –C₆H₄–N(CH₃)₂ (meta) |
| 193 | 0 | H | –C₆H₄–N(CH₃)₂ (ortho) |
| 194 | 0 | –CH₃ | –C₆H₅ |
| 195 | 0 | –CH₃ | –C₆H₄–N(CH₃)₂ |

TABLE 6-continued
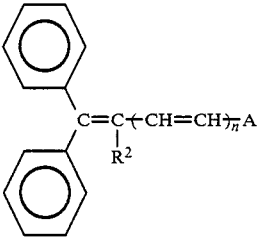
| Compound No. | n | R² | A |
|---|---|---|---|
| 196 | 0 | H | |
| 197 | 0 | H | |
| 198 | 0 | H | |
| 199 | 0 | H | |
| 200 | 0 | H | |
| 201 | 0 | H | |
| 202 | 0 | H | |
| 203 | 0 | H | |

TABLE 6-continued

[Structure: Ph₂C=C(R²)-(CH=CH)ₙ-A]

| Compound No. | n | R² | A |
|---|---|---|---|
| 204 | 0 | H | -C₆H₄-N(CH₂-C₆H₄(OCH₃))₂ (OCH₃ ortho on second ring) |
| 205 | 0 | H | -C₆H₄-N(CH₂-C₆H₄-CH₃)₂ |
| 206 | 0 | H | -C₆H₄-N(CH₂-C₆H₄-CH₃)₂ (CH₃ ortho) |
| 207 | 0 | H | -C₆H₄-N(CH₂-C₆H₄-C₂H₅)₂ |
| 208 | 0 | H | -C₆H₄-N(CH₂-C₆H₄-Cl)₂ |
| 209 | 0 | H | -C₆H₃(CH₃)-N(CH₂-C₆H₄-CH₃)₂ |
| 210 | 0 | H | -C₆H₃(OCH₃)-N(CH₂-C₆H₄-CH₃)₂ |
| 211 | 0 | H | -C₆H₃(OC₂H₅)-N(CH₂-C₆H₄-OCH₃)₂ |
| 212 | 0 | H | -C₆H₃(CH₃)-N(CH₂-C₆H₅)₂ |

TABLE 6-continued
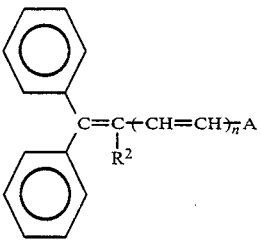
| Compound No. | n | R² | A |
|---|---|---|---|
| 213 | 0 | H | 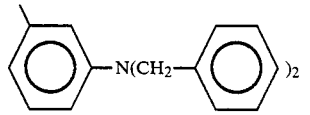 |
| 214 | 0 | H | 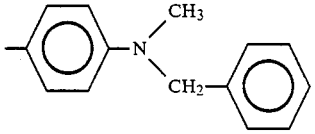 |
| 215 | 0 | H | 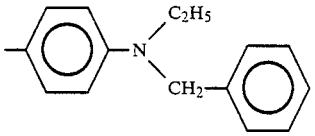 |
| 216 | 0 | H | 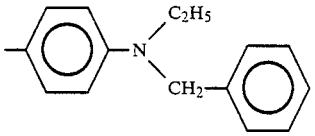 |
| 217 | 0 | H | 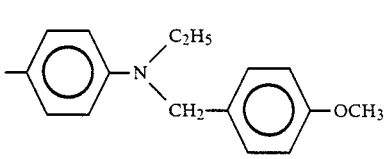 |
| 218 | 0 | H | 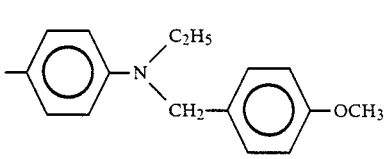 |
| 219 | 0 | H | 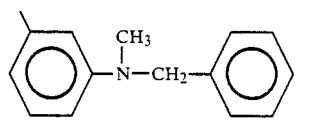 |
| 220 | 0 | H | 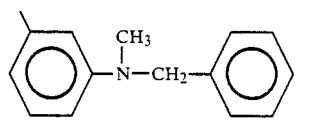 |
| 223 | 0 | H | 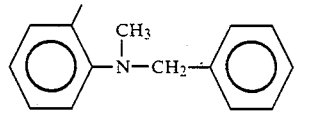 |

TABLE 6-continued
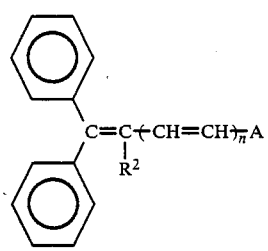
| Compound No. | n | R² | A |
|---|---|---|---|
| 224 | 0 | H | 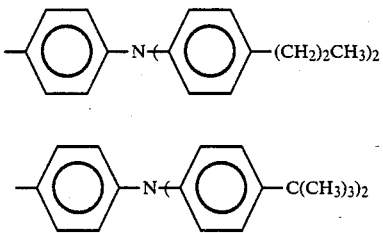 |
| 225 | 0 | H | 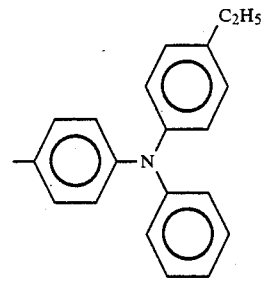 |
| 227 | 0 | H | 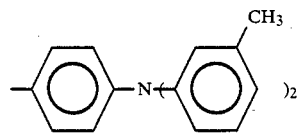 |
| 229 | 0 | H | 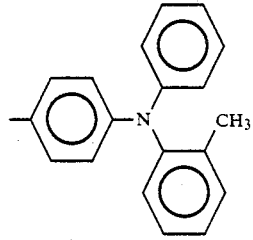 |
| 230 | 0 | H | 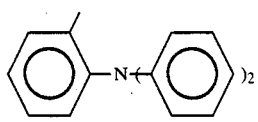 |
| 231 | 0 | H | 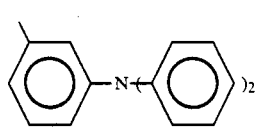 |
| 232 | 0 | H |  |

TABLE 6-continued
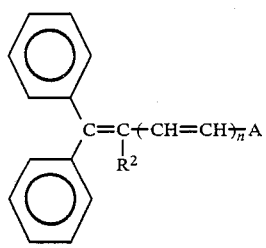
| Compound No. | n | R² | A |
|---|---|---|---|
| 233 | 0 | H | 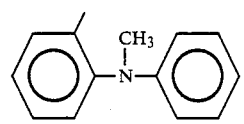 |
| 234 | 0 | H | 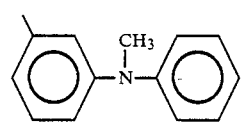 |
| 235 | 0 | H | 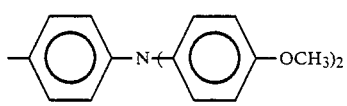 |
| 236 | 0 | H | 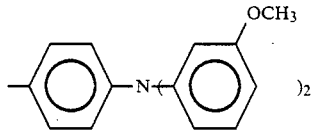 |
| 237 | 0 | H | 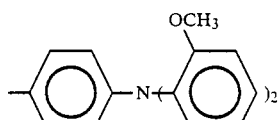 |
| 238 | 0 | H | 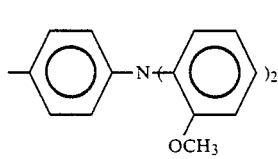 |
| 239 | 0 | H | 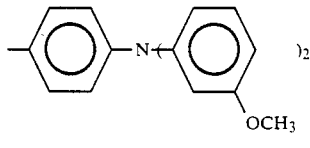 |
| 240 | 0 | H | 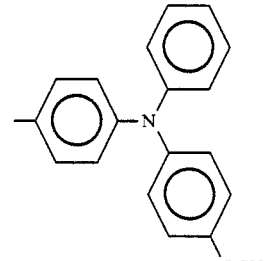 |

TABLE 6-continued
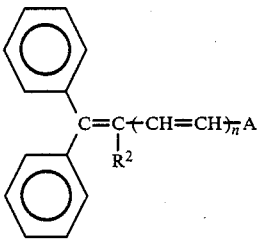
| Compound No. | n | R² | A |
|---|---|---|---|
| 241 | 0 | H | 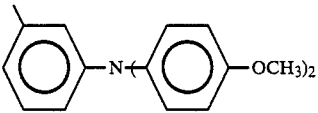 |
| 242 | 0 | H | 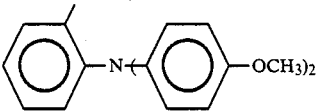 |
| 243 | 0 | H | 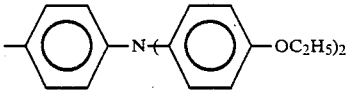 |
| 244 | 0 | H | 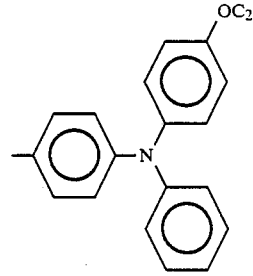 |
| 245 | 0 | H | 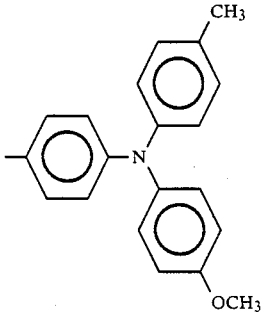 |
| 246 | 0 | H | 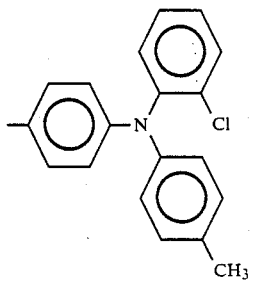 |

TABLE 6-continued
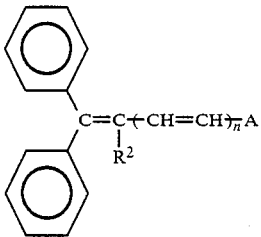
| Compound No. | n | R² | A |
|---|---|---|---|
| 247 | 0 | H | 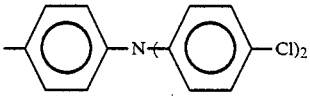 |
| 248 | 0 | H | 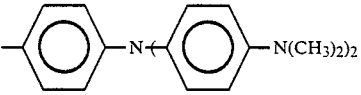 |
| 249 | 0 | H | 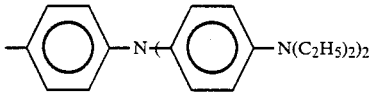 |
| 250 | 0 | H | 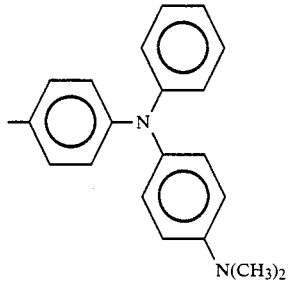 |
| 251 | 0 | H | 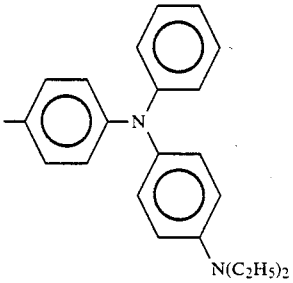 |
| 252 | 0 | H | 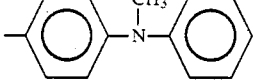 |
| 253 | 0 | H | 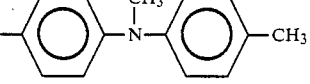 |
| 254 | 0 | H | 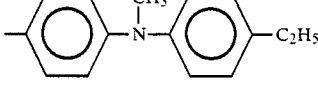 |

TABLE 6-continued
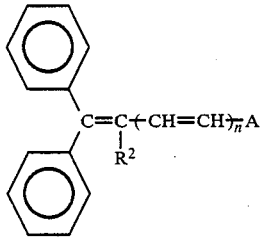
| Compound No. | n | R² | A |
|---|---|---|---|
| 255 | 0 | H | 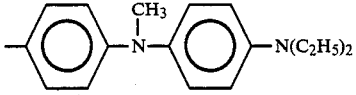 |
| 256 | 0 | H | 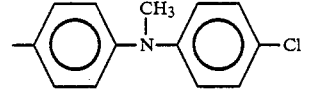 |
| 257 | 0 | H | 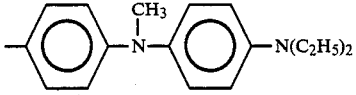 |
| 258 | 0 | H | 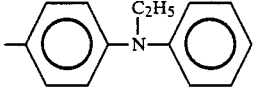 |
| 259 | 0 | H | 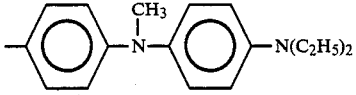 |
| 260 | 0 | H | 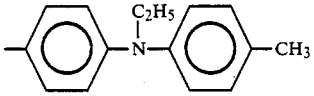 |
| 261 | 0 | H | 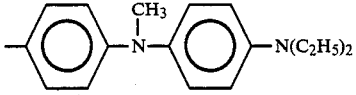 |
| 262 | 0 | H | 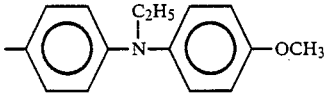 |
| 263 | 0 | H | 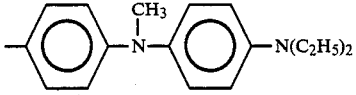 |
| 264 | 0 | H | 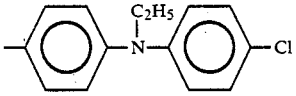 |
| 265 | 0 | H | 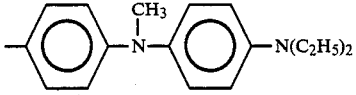 |

TABLE 6-continued
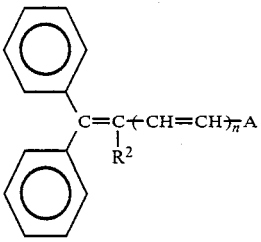
| Compound No. | n | R² | A |
|---|---|---|---|
| 266 | 0 | H | 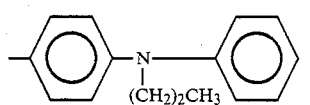 |
| 267 | 0 | H | 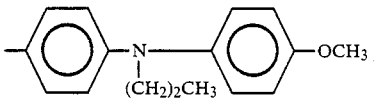 |
| 268 | 0 | H | 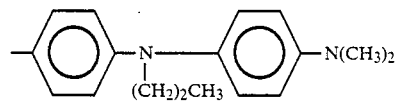 |
| 269 | 0 | H | 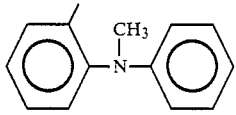 |
| 270 | 0 | H | 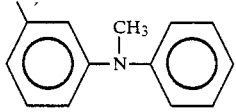 |
| 271 | 0 | H | 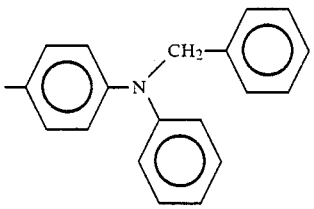 |
| 272 | 0 | H | 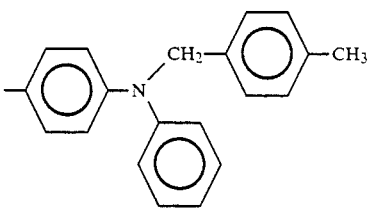 |

TABLE 6-continued
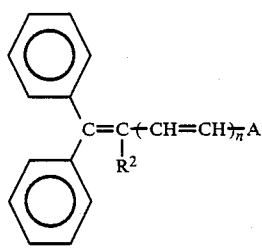
| Compound No. | n | R² | A |
|---|---|---|---|
| 273 | 0 | H | 4-CH₃-C₆H₄-N(C₆H₅)-CH₂-C₆H₄-4-OCH₃ |
| 274 | 0 | H | 4-CH₃-C₆H₄-N(C₆H₅)-CH₂-C₆H₄-2-OCH₃ |
| 275 | 0 | H | 4-CH₃-C₆H₄-N(C₆H₅)-CH₂-C₆H₄-4-OC₂H₅ |
| 276 | 0 | H | 4-CH₃-C₆H₄-N(C₆H₅)-CH₂-C₆H₄-4-Cl |
| 277 | 0 | H | 3-CH₃-C₆H₄-N(C₆H₅)-CH₂-C₆H₅ |

TABLE 6-continued
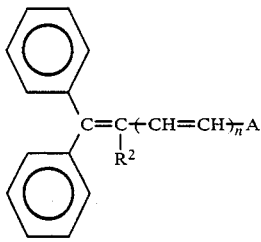
| Compound No. | n | R² | A |
|---|---|---|---|
| 278 | 0 | H | 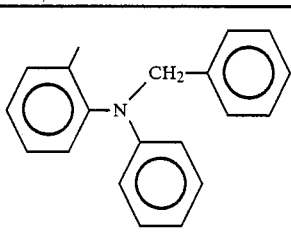 |
| 279 | 0 | H | 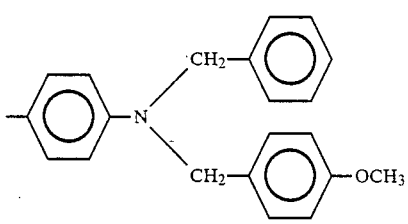 |
| 280 | 0 | H | 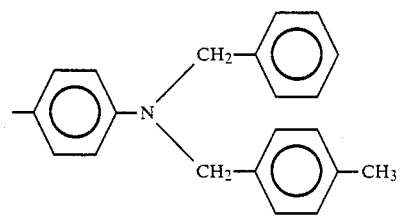 |
| 281 | 0 | H | 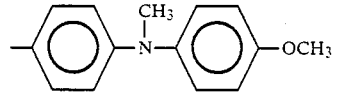 |
| 282 | 0 | H | 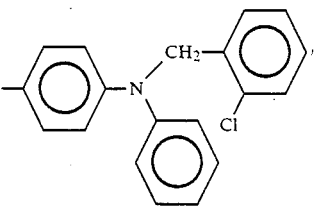 |
| 283 | 0 | H | 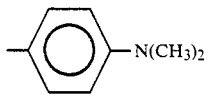 |
| 284 | 0 | H | 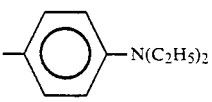 |

TABLE 6-continued
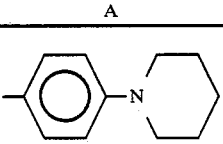
| Compound No. | n | R² | A |
|---|---|---|---|
| 285 | 0 | H | 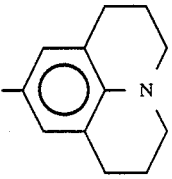 |
| 286 | 0 | H | 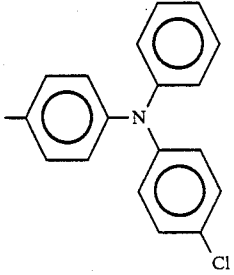 |
| 287 | 0 | H | 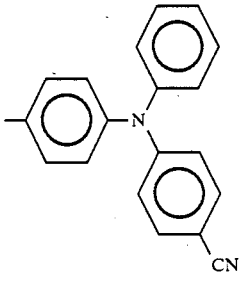 |
| 288 | 0 | H | 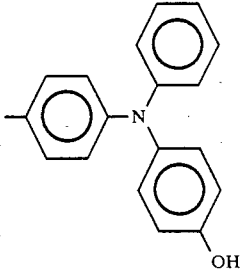 |
| 289 | 0 | H | |

TABLE 6-continued
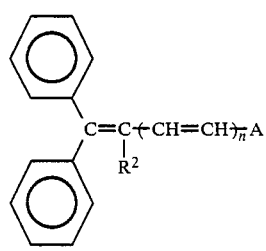
| Compound No. | n | $R^2$ | A |
|---|---|---|---|
| 290 | 0 | H | 4-[N-(4-methylphenyl)-N-phenylamino]benzoic acid group (COOH) |
| 291 | 0 | H | ethyl 4-[N-(4-methylphenyl)-N-phenylamino]benzoate group (COOC$_2$H$_5$) |
| 292 | 0 | H | 4-[N-(4-methylphenyl)-N-phenylamino]nitrobenzene group (NO$_2$) |
| 293 | 0 | H | 4-[N-(3,4-dimethylphenyl)-N-(4-methylphenyl)amino]phenyl group (CH$_3$, CH$_3$, CH$_3$) |

TABLE 6-continued
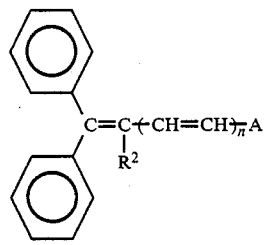
| Compound No. | n | $R^2$ | A |
|---|---|---|---|
| 294 | 0 | H | 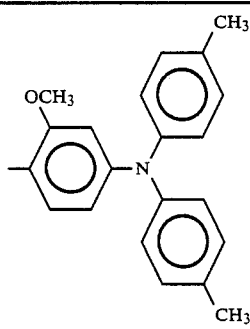 |
| 295 | 0 | H | 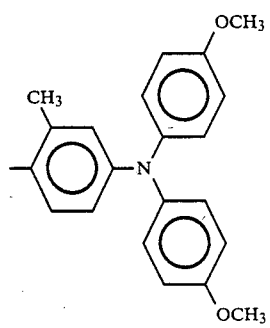 |
| 296 | 0 | H | 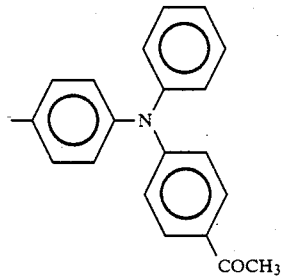 |
| 297 | 0 | H | 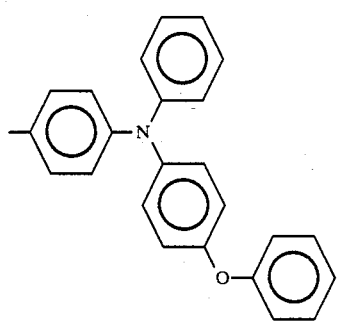 |

TABLE 6-continued

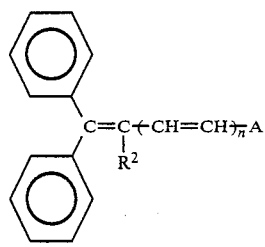

| Compound No. | n | R² | A |
|---|---|---|---|
| 298 | 0 | H | —⟨⟩—N(CH₃)₂ |
| 299 | 0 | H | —⟨⟩—N(C₂H₅)₂ |
| 300 | 1 | H | —⟨⟩ (OCH₃) |
| 301 | 0 | H | —⟨⟩—N(⟨⟩)(⟨⟩-CH₃, CH₃) |

When an electrophotographic photoconductor according to the present invention as shown in FIG. 1 is prepared, at least one of the above prepared stilbene compounds is dispersed in a binder resin solution, and a sensitizer dye is then added to the mixture, and the thus prepared photosensitive liquid is coated on an electroconductive support material 1 and dried, so that a photosensitive layer 2a is formed on the electroconductive support material 1.

It is preferably that the thickness of the photosensitive layer 2a be in the range of about 3 μm to about 50 μm, more preferably in the range of about 5 μm to about 20 μm. It is preferable that the amount of the stilbene compound contained in the photosensitive layer 2a be in the range of about 30 wt. % to about 70 wt. % of the total weight of the photosensitive layer 2a, more preferably about 50 wt. % of the total weight of the photosensitive layer 2a. Further, it is preferable that the amount of the sensitizer dye contained in the photosensitive layer 2a be in the range of about 0.1 wt. % to about 5 wt. % of the total weight of the photosensitive layer 2a, more preferably in the range of about 0.5 wt. % to about 3 wt. %, of the total weight of the photosensitive layer 2a.

As the sensitizer dye, the following can be employed in the present invention: Triarylmethane dyes, such as Brilliant Green, Victoria Blue B, Methyl Violet, Crystal Violet, and Acid Violet 6B; xanthene dyes, such as Rhodamine B, Rhodamine 6G, Rhodamine G Extra, Eosin S, Erythrosin, Rose Bengale, and Fluorescein; thiazine dyes, such as Methylene Blue; cyanin dyes such as cyanin; and pyrylium dyes, such as 2,6-diphenyl-4-(N,N-dimethylaminophenyl) thiapyrylium perchlorate and benzopyrylium salt (Japanese Patent Publication 48-25658). These sensitizer dyes can be used alone or in combination.

An electrophotographic photoconductor according to the present invention as shown in FIG. 2 can be prepared, for example, as follows. A charge generating material in the form of small particles is dispersed in a solution of one or more stilbene compounds and a binder agent. The thus prepared dispersion is coated on the electroconductive support material 1 and is then dried, whereby a photosensitive layer 2b is formed on the electroconductive support material 1.

It is preferable that the thickness of the photosensitive layer 2b be in the range of about 3 μm to about 50 μm, more preferably in the range of about 5 μm to about 20 μm. It is preferable that the amount of stilbene compound contained in the photosensitive layer 2b be in the range of about 10 wt. % to about 95 wt. %, more preferably in the range of about 30 wt. % to about 90 wt. % of the total weight of the photosensitive layer 2b. Further, it is preferable that the amount of the charge generating material 3 contained in the photosensitive layer 2b be in the range of about 0.1 wt. % to about 50 wt. %, more preferably in the range of about 1 wt. % to about 20 wt. %, of the total weight of the photosensitive layer 2b.

As the charge generating material 3, the following can be employed in the present invention: Inorganic pigments, such as selenium, a selenium-tellurium alloy, cadmium sulfide, a cadmium sulfide-selenium alloy, and —silicon; and organic pigments, such as C.I. Pigment Blue 25 (C.I. 21180), C.I. Pigment Red 41 (C.I. 21200), C.I. Acid Red 52 (C.I. 45100), and C.I. Basic Red 3 (C.I. 45210); an azo pigment having a carbazole skeleton (Japanese Laid-Open patent application 53-95033), an azo dye having a distyrylbenzene skeleton (Japanese Laid-Open patent application 53-133445), an azo pigment having a triphenylamine skeleton (Japanese Laid-Open Paten Application 53-132347), an azo pigment having a dibenzothiophene skeleton (Japanese Laid-Open patent application 54-21728), an azo pigment having an oxazole skeleton (Japanese Laid-Open patent application 54-12742), an azo pigment having a fluorenon skeleton (Japanese Laid-Open patent application 54-22834), an azo pigment having a bisstilbene skeleton (Japanese Laid-Open patent application 54-17733), an azo pigment having a distyryl oxadiazole skeleton (Japanese Laid-Open patent application 54-2129), an azo dye having a distyryl carbazole skeleton (Japanese Laid-Open patent application 54-14967); phthalocyanine-type pigment such as C.I. Pigment Blue 16 (C.I. 74100); Indigo-type pigments such as C.I. Vat Brown 5 (C.I. 73410) and C.I. Vat Dye (C.I. 73030); and perylene-type pigments, such as Algo Scarlet B (made by Bayer Co., Ltd.) and Indanthrene Scarlet R (made by Bayer Co., Ltd). These charge generating materials can be used alone or in combination.

The photoconductor according to the present invention as shown in FIG. 3 can be prepared, for example, as follows. A charge generating material is vacuum-evaporated on the electroconductive support material 1, or a charge generating material in the form of fine particles is dispersed in a solution of a binder agent. This dispersion is applied to the electroconductive support material 1 and then dried, and, if necessary, the applied layer is subjected to buffing to make the surface smooth or to adjust the thickness of the layer to a predetermined thickness, whereby a charge generating layer 5 is formed. A charge transporting layer 6 is then formed on the charge generating layer 5 by applying a solution of one or more stilbene compounds and a binder agent to the charge generating layer 5 and then drying. In this photoconductor, the charge generating material employed is the same as that employed in the photoconductor shown in FIG. 2. It is preferable that the thickness of the charge generating layer 5 be less than about 5 μm, more preferably less than about 2 μm. It is preferable that the thickness of the charge transporting layer 6 be in the range of about 3 μm to about 50 μm, more preferably in the range of about 5 μm to about 20 μm. In the case where the charge generating layer 5 comprises a charge generating material in the form of fine particles, dispersed in a binder agent, it is preferable that the amount of the charge generating material in the charge generating layer 5 be in the range of about 10 wt. % to about 95 wt. % of the entire weight of the charge generating layer 5, more preferably in the range of about 50 wt. % to about 90 wt. %. Further, it is preferable that the amount of the stilbene compound contained in the charge transporting layer 6 be in the range of about 10 wt. % to about 95 wt. %, more preferably in the range of about 30 wt. % to about 90 wt. % of the total weight of the charge transporting layer 6.

As the electroconductive support material 1 for use in the present invention, a metal plate or metal foil, for example, made of aluminum, a plastic film on which a metal, for example, aluminum, is evaporated, or paper which has been treated so as to be electroconductive, can be employed.

As the binder agent for use in the present invention, condensation resins, such as polyamide polyurethane polyester, epoxy resin, polyketone and polycarbonate; and vinyl polymers, such as polyvinylketone, polystyrene, poly-N-vinylcarbazole and polyacrylamide, can be used.

Other conventional electrically insulating and adhesive resins can be used as the binder agent in the present invention. When necessary, there can be added to the binder resins a plasticizer, for example, halogenated paraffin, polybiphenyl chloride, dimethylnaphthalene and dibutyl phthalate.

In the above described photoconductors according to the present invention, if necessary, an adhesive or barrier layer can be disposed between the electroconductive support material and the photosensitive layer. The adhesive layer or the barrier layer can be made of, for example, polyamide, nitrocellulose, or aluminum oxide. It is preferable that the thickness of the adhesive layer or barrier layer be about 1 μm or less.

When copying is performed by use of the photoconductors according to the present invention, the surface of the photoconductor is charged uniformly in the dark to a predetermined polarity. The uniformly charged photoconductor is exposed to a light image so that a latent electrostatic image is formed on the photoconductor. The thus formed latent electrostatic image is developed by a developer to a visible image, and, when necessary, the developed image can be transferred to a sheet of paper. The photoconductors according to the present invention have high photosensitivity and excellent flexibility.

Preparation of embodiments of an electrophotographic photoconductors according to the present invention will now be explained in detail by referring to the following examples:

EXAMPLE P-1

The following components were ground and dispersed in a ball mill to prepare a charge generating layer formation liquid:

| | Parts by Weight |
|---|---|
| Diane Blue (C.I. Pigment Blue 25, C.I. 21180) (a charge generating pigment) of the following formula (CG-1) | 76 |
| 2% tetrahydrofuran solution of a polyester resin (Vylon 200 made by Toyobo Co., Ltd.) | 1,260 |
| Tetrahydrofuran | 3,000 |

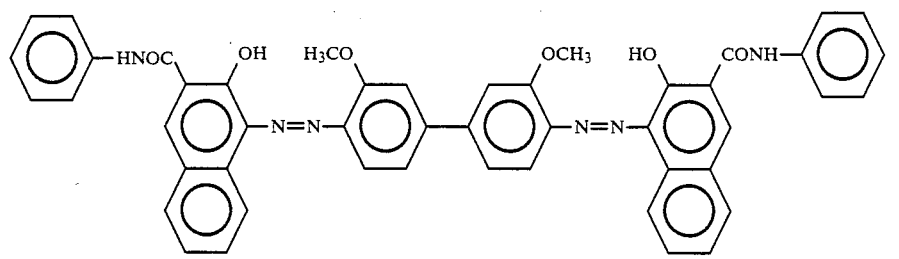

(CG-1)

The charge generating layer formation liquid was coated by a doctor blade on the aluminum-evaporated surface of an aluminum-evaporated polyester base film, which served as an electroconductive support material, so that a charge generating layer, with a thickness of about 1 μm when dried at room temperature, was formed on the electroconductive support material.

Then the following components were mixed and dissolved, and a charge transporting layer formation liquid was prepared:

| | Parts by Weight |
|---|---|
| 4-N,N—diphenylaminostilbene (Prepared in Example 1; the stilbene compound No. 61 in Table 3) | 2 |
| Polycarbonate resin (Panlite K 1300 made by Teijin Limited.) | 2 |
| Tetrahydrofuran | 16 |

The thus prepared charge transporting layer formation liquid was coated on the aforementioned charge generating layer by a doctor blade and was dried at 80° C. for 2 minutes and then at 105° C. for 5 minutes, so that a charge transporting layer with a thickness of about 20 μm was formed on the charge generating layer; thus, an electrophotographic photoconductor No. 1 according to the present invention was prepared.

The electrophotographic photoconductor No. 1 was charged negatively in the dark under application of −6 kV of corona charge for 20 seconds and was then allowed to stand in the dark for 20 seconds without applying any charge thereto. At this moment, the surface potential Vpo (V) of the photoconductor was measured by a Paper Analyzer (Kawaguchi Electro Works, Model SP-428). The photoconductor was then illuminated by a tungsten lamp in such a manner that the illuminance on the illuminated surface of the photoconductor was 20 lux, and the exposure $E_{\frac{1}{2}}$ (lux. seconds) required to reduce the initial surface potential Vpo (V) to $\frac{1}{2}$ the initial surface potential Vpo (V) was measured. The results showed that Vpo (V)=−1340 V and $E_{\frac{1}{2}}$=2.9 lux·seconds.

EXAMPLE P-2

Example P-1 was repeated except that the charge generating pigment of the formula CG-1 employed in Example P-1 was replaced by a charge generating pigment of the following formula CG-2, whereby an electrophotographic photoconductor No. 2 according to the present invention was prepared.

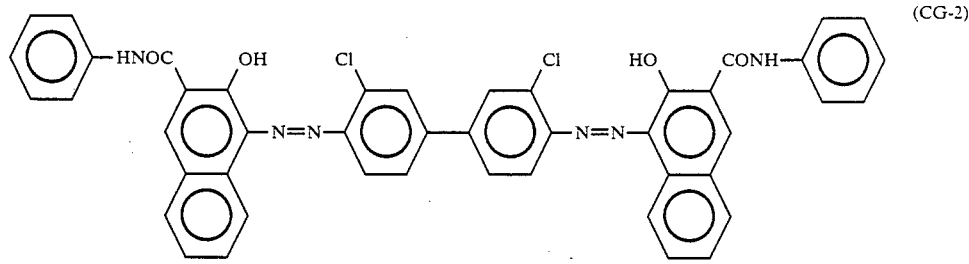

(CG-2)

As in the case of Example P-1, the electrophotographic photoconductor was charged negatively in the dark under application of −6 kV of corona charge for 20 seconds, and was then allowed to stand in the dark for 20 seconds without applying any charge thereto, and, as in the case of Example P-1, Vpo and $E_{\frac{1}{2}}$ were measured. The results showed that Vpo=−1100 V and $E_{\frac{1}{2}}$=2.1 lux·seconds.

EXAMPLE P-3

Example P-1 was repeated except that the charge generating pigment of the formula CG-1 employed in Example P-1 was replaced by a charge generating pigment of the following formula CG-3, whereby an electrophotographic photoconductor No. 3 according to the present invention was prepared.

EXAMPLE P-5

Example P-1 was repeated except that the charge generating pigment of the formula CG-1 employed in Example P-1 was replaced by a charge generating pigment of the following formula CG-5, whereby an electrophotographic photoconductor No. 5 according to the present invention was prepared.

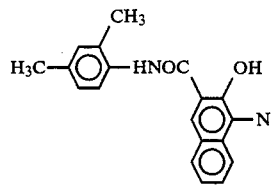
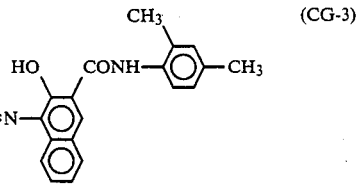

Vpo and $E_{\frac{1}{2}}$ were measured. The results showed that Vpo = $-1210$ V and $E_{\frac{1}{2}}=1.3$ lux·seconds.

EXAMPLE P-4

Example P-1 was repeated except that the charge generating pigment of the formula CG-1 employed in Example P-1 was replaced by a charge generating pigment of the following formula CG-4, whereby an electrophotographic photoconductor No. 4 according to the present invention was prepared.

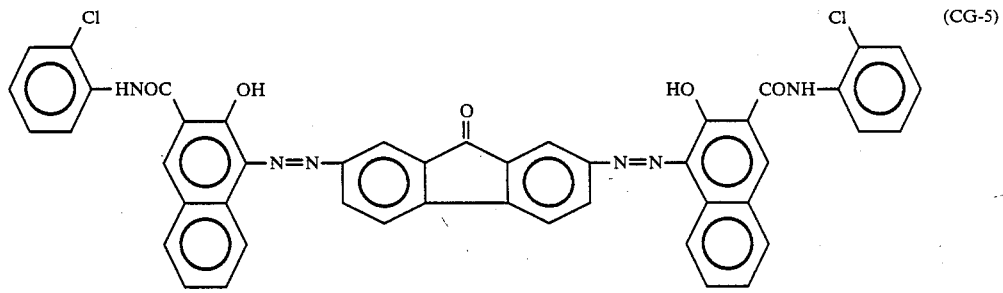

Vpo and $E_{\frac{1}{2}}$ were measured. The results showed that Vpo = $-1100$ V and $E_{\frac{1}{2}}=0.9$ lux·seconds.

EXAMPLE P-6

Example P-1 was repeated except that the charge generating pigments of the formula CG-1 employed in Example P-1 was replaced by a charge generating pigment of the following formula CG-6, whereby an electrophotographic photoconductor No. 6 according to the present invention was prepared.

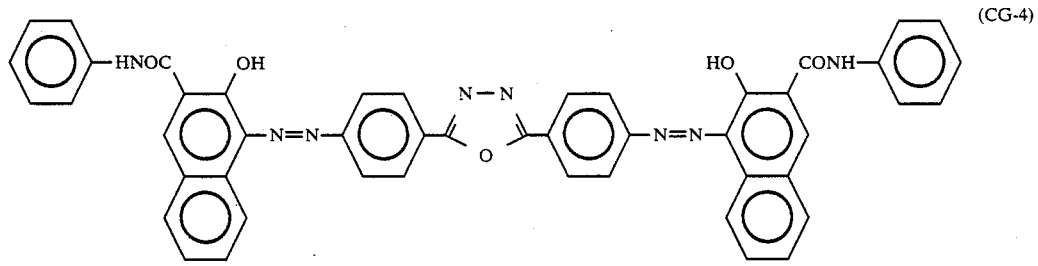

Vpo and $E_{\frac{1}{2}}$ were measured. The results showed that Vpo = $-1290$ V and $E_{\frac{1}{2}}=3.9$ lux·seconds.

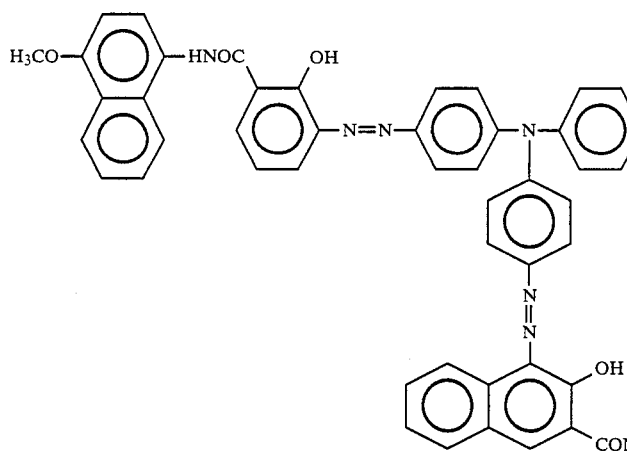
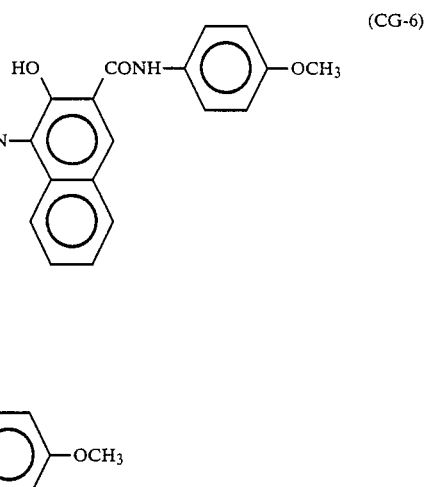

(CG-6)

Vpo and $E_{178}$ were measured. The results showed that Vpo = -1040 V and $E_{\frac{1}{2}}$ = 1.2 lux·seconds.

EXAMPLE P-7

Example P-1 was repeated except that the charge generating pigment of the formula CG-1 employed in Example P-1 was replaced by β-type copper phthalocyanine as a charge generating pigment, whereby an electrophotographic photoconductor No. 7 according to the present invention was prepared.

Vpo and $E_{\frac{1}{2}}$ were measured. The results showed that Vpo = -980 V and $E_{\frac{1}{2}}$ = 2.5 lux·seconds.

EXAMPLES P-8 THROUGH P-35

Example P-1 was repeated except that the charge generating material and the charge transporting material (stilbene compounds) employed in Example P-1 were respectively replaced by the charge generating materials and the charge transporting materials (stilbene compounds) listed in Table 7, whereby electrophotographic photoconductive No. 8 through No. 35 according to the present invention were prepared.

$V_{po}$ and $E_{\frac{1}{2}}$ of each electrophotographic photoconductor are also shown in Table 7.

EXAMPLE P-36

Selenium was vacuum-evaporated with a thickness of approximately 1.0 μm on an approximately 300 μm thick aluminum plate so that a charge generating layer was formed on the aluminum plate.

A charge transporting layer liquid was prepared by mixing and dispersing the following components:

| | Parts by Weight |
|---|---|
| Stilbene compound No. 61 (prepared in Example 1 and the same as that employed in Example P-1) | 2 |
| Polyester resin (Polyester Adhesive 49000 made by Dupont Co.) | 3 |
| Tetrahydrofuran | 45 |

The thus prepared charge transporting layer liquid was coated on the aforementioned selenium charge generating layer by a doctor blade, dried at room temperature and then dried under reduced pressure, so that a charge transporting layer about 10 μm thick was formed on the charge generating layer; thus, an electrophotographic photoconductor No. 36 according to the present invention was prepared.

Vpo and $E_{\frac{1}{2}}$ were measured. The results showed that Vpo = -1110 V and $E_{\frac{1}{2}}$ = 2.5 lux·seconds.

EXAMPLE P-37

A perylene pigment C.I. Vat Red 23 (C.I. 71130) of the following formula was vacuum-evaporated with a thickness of about 0.3 μm on an approximately 300 μm thick aluminum plate so that a charge generating layer was formed.

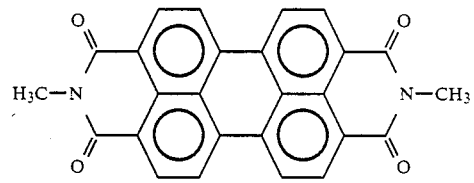

A charge transporting layer liquid was prepared by mixing and dispersing the following components:

| | Parts by Weight |
|---|---|
| Stilbene compound No. 1 (prepared in Example 2) | 2 |
| Polyester resin (Polyester Adhesive 49000 made by Dupont Co.) | 3 |
| Tetrahydrofuran | 45 |

The thus prepared charge transporting layer liquid was coated on the aforementioned selenium charge generating layer by a doctor blade, dried at room temperature and then dried under reduced pressure, whereby a charge transporting layer about 10 μm thick was formed on the charge generating layer; thus, an electrophotographic photoconductor No. 37 according to the present invention was prepared.

Vpo and $E_{\frac{1}{2}}$ were measured. The results showed that Vpo = -1200 V and $E_{\frac{1}{2}}$ = 4.3 lux·seconds.

EXAMPLE P-38

One part by weight of Diane Blue (C.I. Pigment Blue 25, C.I. 21180) which was the same as that employed in Example P-1 was added to 158 parts by weight of tetrahydrofuran, and the mixture was ground and dispersed in a ball mill. To this mixture, 12 parts by weight of stilbene compound No. 61 and 18 parts by weight of a polyester resin (Polyester Adhesive 49000 made by Dupont Co.) were added and mixed, whereby a photosensitive layer formation liquid was prepared.

The thus prepared photosensitive layer formation liquid was coated on an aluminum-evaporated polyester film by a doctor blade and was dried at 100° C. for 30 minutes, so that a photosensitive layer with a thickness of about 16 μm was formed on the aluminum-evaporated polyester film, thus, an electrophotographic photoconductor No. 38 according to the present invention was prepared.

The electrophotographic photoconductor No. 38 was charged positively in the dark under application of +6 kV of corona charge for 20 seconds and was then allowed to stand in the dark for 20 seconds without applying any charge thereto. At this moment, the surface potential Vpo (V) of the photoconductor was measured by a Paper Analyzer (Kawaguchi Electro Works, Model SP-428). The photoconductor was then illuminated by a tungsten lamp in such a manner that the illuminance on the illuminated surface of the photoconductor was 20 lux, so that the exposure $E_{\frac{1}{2}}$ (lux seconds) required to reduce the initial surface potential Vpo (V) to ½ the initial surface potential Vpo (V) was measured. The results showed that Vpo (V)=+950 V and $E_{\frac{1}{2}}$=2.4 lux·seconds.

The charge generating material, the charge transporting material, $V_{po}$ and $E_{\frac{1}{2}}$ of each of the electrophotographic photoconductors No. 1 through No. 38 are summarized in the following Table 7:

TABLE 7

| Photo-Conductor | Charge Generating Material | Charge Transporting Material (Stilbene Compound) | $V_{po}$ (V) | $E_{\frac{1}{2}}$ (lux · seconds) |
|---|---|---|---|---|
| No. 1 | CG-1 | No. 61 | −1340 | 2.9 |
| No. 2 | CG-2 | No. 61 | −1100 | 2.1 |
| No. 3 | CG-3 | No. 61 | −1210 | 1.3 |
| No. 4 | CG-4 | No. 61 | −1290 | 3.9 |
| No. 5 | CG-5 | No. 61 | −1100 | 0.9 |
| No. 6 | CG-6 | No. 61 | −1040 | 1.2 |
| No. 7 | β-type Copper Phthalocyanine | No. 61 | −980 | 2.5 |
| No. 8 | CG-1 | No. 1 | −1200 | 2.8 |
| No. 9 | CG-2 | No. 1 | −990 | 2.6 |
| No. 10 | CG-3 | No. 1 | −1020 | 2.2 |
| No. 11 | CG-5 | No. 1 | −870 | 1.7 |
| No. 12 | CG-3 | No. 154 | −1070 | 2.1 |
| No. 13 | CG-5 | No. 154 | −630 | 1.2 |
| No. 14 | CG-3 | No. 8 | −1050 | 2.2 |
| No. 15 | CG-5 | No. 8 | −920 | 1.8 |
| No. 16 | CG-3 | No. 62 | −1100 | 1.3 |
| No. 17 | CG-5 | No. 62 | −930 | 0.8 |
| No. 18 | CG-3 | No. 2 | −1080 | 2.2 |
| No. 19 | CG-5 | No. 2 | −690 | 1.9 |
| No. 20 | CG-3 | No. 12 | −980 | 1.5 |
| No. 21 | CG-5 | No. 18 | −1210 | 1.2 |
| No. 22 | CG-3 | No. 18 | −1020 | 1.6 |
| No. 23 | CG-5 | No. 18 | −1130 | 1.6 |
| No. 24 | CG-3 | No. 121 | −1050 | 1.8 |
| No. 25 | CG-5 | No. 121 | −990 | 1.1 |
| No. 26 | CG-3 | No. 68 | −1300 | 1.2 |
| No. 27 | CG-5 | No. 68 | −780 | 0.7 |
| No. 28 | CG-3 | No. 100 | −1460 | 1.4 |
| No. 29 | CG-5 | No. 100 | −1110 | 1.3 |
| No. 30 | CG-3 | No. 88 | −440 | 1.1 |
| No. 31 | CG-5 | No. 88 | −770 | 0.7 |
| No. 32 | CG-3 | No. 160 | −1440 | 1.4 |
| No. 33 | CG-5 | No. 160 | −1430 | 3.9 |
| No. 34 | CG-3 | No. 161 | −680 | 1.2 |
| No. 35 | CG-5 | No. 161 | −1160 | 1.0 |
| No. 36 | Se | No. 61 | −1110 | 2.5 |
| No. 37 | Perylene Pigment | No. 1 | −1200 | 4.3 |
| No. 38 | CG-1 | No. 61 | +950 | 2.4 |

Each of the electrophotographic photoconductors prepared in Examples P-1 through P-37 was negatively charged, while the electrophotographic photoconductor prepared in Example P-38 was positively charged, by a commercially available copying machine, so that a latent electrostatic image was formed on each photoconductor and was developed with a dry type developer. The developed images were transferred to a high quality transfer sheet and were fixed to the transfer sheet. As a result, clear images were obtained from each of the electrophotographic photoconductors.

When a wet type developer was used instead of the dry type developer, a clear image was also obtained from each of the electrophotographic photoconductors.

EXAMPLE P-39

Example P-1 was repeated except that the stilbene compound No. 61 employed in Example P-1 was replaced by α-phenylstilbene compound No. 219 in Table 6, of the following formula, prepared in Example 28, whereby an electrophotographic photoconductor No. 39 was prepared.

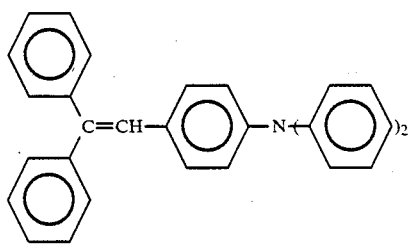

(Stilbene Compound No. 219)

EXAMPLES P-40 THROUGH P-77

Example P-1 was repeated except that the charge generating material and the charge transporting material employed in Example P-1 were respectively replaced by the charge generating materials and charge transporting materials (stilbene compounds) listed in Table 8, whereby electrophotographic photoconductors No. 40 through No. 77 according to the present invention was prepared.

EXAMPLE P-78

Example P-36 was repeated except that the stilbene compound No. 61 employed in Example P-36 was replaced by the α-phenylstilbene compound No. 219 in Table 6, whereby an electrophotographic photoconductor No. 78 according to the present invention was prepared.

EXAMPLE P-79

Example P-37 was repeated except that the stilbene compound No. 1 employed in Example P-37 was replaced by the α-phenylstilbene compound No. 182 in Table 6, of the following formula, prepared in Example 30, whereby an electrophotographic photoconductor No. 79 was prepared.

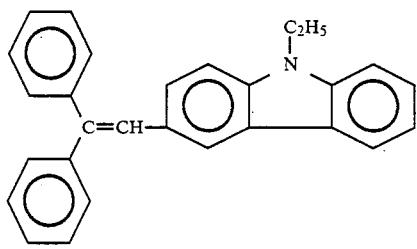

(Stilbene Compound No. 182)

EXAMPLE P-80

Example P-38 was repeated except that the stilbene compound employed in Example P-38 was replaced by the α-phenylstilbene compound No. 219 employed in Example P-78, of the following formula, whereby an electrophotographic photoconductor No. 80 according to the present invention was prepared.

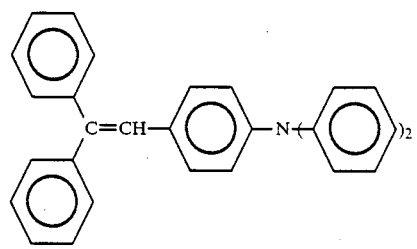

(Stilbene Compound No. 219)

Those electrophotographic photoconductors were charged negatively or positively under application of −6 KV or +6 KV of corona charge exactly in the same manner as in the case of Example P-1, and $V_{po}$ and $E_{\frac{1}{2}}$ of each electrophotographic photoconductor were measured. The results are shown in Table 8.

TABLE 8

| Photo-Conductor | Charge Generating Material | Charge Transporting Material (Stilbene Compound) | $V_{po}$ (V) | $E_{\frac{1}{2}}$ (lux · seconds) |
|---|---|---|---|---|
| No. 39 | CG-1 | No. 219 | −1120 | 3.0 |
| No. 40 | CG-2 | No. 219 | −990 | 2.5 |

TABLE 8-continued

| Photo-Conductor | Charge Generating Material | Charge Transporting Material (Stilbene Compound) | $V_{po}$ (V) | $E_{\frac{1}{2}}$ (lux · seconds) |
|---|---|---|---|---|
| No. 41 | CG-3 | No. 219 | −1170 | 1.3 |
| No. 42 | CG-4 | No. 219 | −1290 | 4.1 |
| No. 43 | CG-5 | No. 219 | −1090 | 0.9 |
| No. 44 | CG-6 | No. 219 | −980 | 1.2 |
| No. 45 | β-type Copper Phthalocyanine | No. 219 | −820 | 2.7 |
| No. 46 | CG-1 | No. 182 | −1200 | 3.4 |
| No. 47 | CG-2 | No. 182 | −1100 | 2.4 |
| No. 48 | CG-3 | No. 182 | −1070 | 2.2 |
| No. 49 | CG-5 | No. 182 | −890 | 1.5 |
| No. 50 | CG-3 | No. 299 | −1350 | 1.3 |
| No. 51 | CG-5 | No. 299 | −1060 | 1.1 |
| No. 52 | CG-3 | No. 174 | −980 | 1.4 |
| No. 53 | CG-5 | No. 174 | −600 | 1.0 |
| No. 54 | CG-3 | No. 202 | −1210 | 2.1 |
| No. 55 | CG-5 | No. 202 | −1070 | 1.4 |
| No. 56 | CG-3 | No. 196 | −1280 | 1.3 |
| No. 57 | CG-5 | No. 196 | −1170 | 1.1 |
| No. 58 | CG-3 | No. 220 | −1280 | 1.2 |
| No. 59 | CG-5 | No. 220 | −1130 | 0.8 |
| No. 60 | CG-3 | No. 181 | −1310 | 2.4 |
| No. 61 | CG-5 | No. 181 | −1040 | 4.5 |
| No. 62 | CG-3 | No. 179 | −1250 | 3.1 |
| No. 63 | CG-5 | No. 179 | −1000 | 2.9 |
| No. 64 | CG-3 | No. 177 | −1390 | 1.5 |
| No. 65 | CG-5 | No. 177 | −1140 | 2.6 |
| No. 66 | CG-3 | No. 235 | −350 | 0.7 |
| No. 67 | CG-5 | No. 235 | −600 | 0.6 |
| No. 68 | CG-3 | No. 240 | −540 | 1.3 |
| No. 69 | CG-5 | No. 240 | −980 | 0.9 |
| No. 70 | CG-3 | No. 226 | −990 | 1.2 |
| No. 71 | CG-5 | No. 226 | −1100 | 1.0 |
| No. 72 | CG-3 | No. 287 | −1300 | 1.4 |
| No. 73 | CG-5 | No. 287 | −1210 | 1.5 |
| No. 74 | CG-3 | No. 288 | −850 | 1.3 |
| No. 75 | CG-5 | No. 288 | −1400 | 4.4 |
| No. 76 | CG-3 | No. 301 | −680 | 1.2 |
| No. 77 | CG-5 | No. 301 | −1100 | 1.0 |
| No. 78 | Se | No. 219 | −1120 | 2.8 |
| No. 79 | Perylene Pigment | No. 182 | −1300 | 4.8 |
| No. 80 | CG-1 | No. 219 | +1220 | 4.7 |

Each of the electrophotographic photoconductors prepared in Examples P-39 through P-79 was negatively charged, while the electrophotographic photoconductor prepared in Example P-80 was positively charged, by a commercially available copying machine, and a latent electrostatic image was formed on each photoconductor and was developed with a dry type developer. The developed image was transferred to a high quality transfer sheet and was fixed to the transfer sheet. As a result, a clear image was obtained from each of the electrophotographic photoconductors. When a wet type developer was used instead of the dry type developer, a clear image was also obtained from each electrophotographic photoconductor.

What is claimed is:

1. A compound having the formula

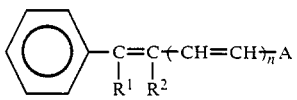

wherein n is 0 or 1, $R^2$ is hydrogen, alkyl or phenyl; the pair ($R^1$, A) is selected from the group consisting of (a) $R^1$ is hydrogen, A is

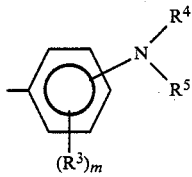

(b) $R^1$ is

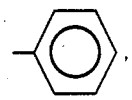

A is selected from the group consisting of

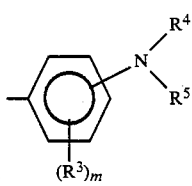

N-alkyl carbazolyl, and substituted N-alkyl carbazolyl, and (c) $R^1$ is hydrogen or

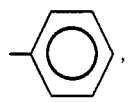

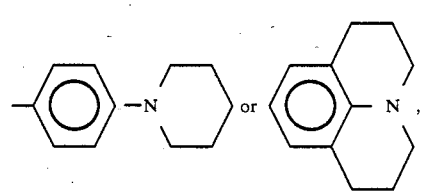

wherein $R^3$ is hydrogen alkyl, alkoxy, or halogen, and $R^4$ and $R^5$ independently represent alkyl, aryl, substituted aryl, aralkyl and substituted aralkyl, and m is an integer of from 0 to 2, provided that when $R^1$ is hydrogen and n is 1, $R^2$ is not hydrogen.

2. A compound having the formula

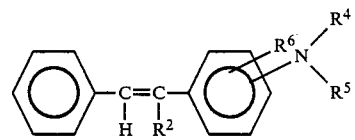

wherein $R^2$ is hydrogen, alkyl or phenyl, $R^4$ and $R^5$ independently are alkyl, aryl, substituted aryl, aralkyl or substituted aralkyl, and $R^6$ is hydrogen, alkyl, alkoxy or halogen.

3. A compound as claimed in claim 2 in which $R^4$ and $R^5$ are benzyl or substituted benzyl.

4. A compound as claimed in claim 2 in which $R^4$ is alkyl and $R^5$ is benzyl or substituted benzyl.

5. A compound as claimed in claim 2 in which $R^4$ and $R^5$ are phenyl or substituted phenyl.

6. A compound as claimed in claim 2 in which $R^4$ is alkyl and $R^5$ is phenyl or substituted phenyl.

7. A compound as claimed in claim 2 in which $R^4$ is benzyl or substituted benzyl, and $R^5$ is phenyl or substituted phenyl.

8. A compound having the formula

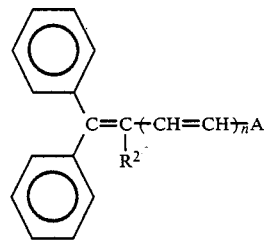

wherein n is 0 or 1, $R^2$ is hydrogen, alkyl, or phenyl, and A is selected from the group consisting of

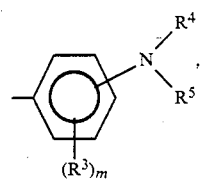

N-alkyl carbazolyl, and substituted N-alkyl carbazolyl, $R^3$ is hydrogen, alkyl, alkoxy or halogen, $R^4$ and $R^5$ independently are alkyl, aryl, substituted aryl, aralkyl or substituted aralkyl, and m is an integer of from 0 to 2.

9. A compound as claimed in claim 8 in which $R^4$ and $R^5$ are benzyl or substituted benzyl.

10. A compound as claimed in claim 8 in which $R^4$ is alkyl and $R^5$ is benzyl or substituted benzyl.

11. A compound as claimed in claim 8 in which $R^4$ and $R^5$ are phenyl or substituted phenyl.

12. A compound as claimed in claim 8 in which $R^4$ is alkyl and $R^5$ is phenyl or substituted phenyl.

13. A compound as claimed in claim 8 in which $R^4$ is benzyl or substituted benzyl, and $R^5$ is phenyl or substituted phenyl.

* * * * *

UNITED STATES PATENT AND TRADEMARK OFFICE
CERTIFICATE OF CORRECTION

PATENT NO. : 4,892,949
DATED : January 9, 1990
INVENTOR(S) : Masaomi SASAKI

It is certified that error appears in the above-identified patent and that said Letters Patent is hereby corrected as shown below:

Column 109, lines 50-55; change to read as follows:

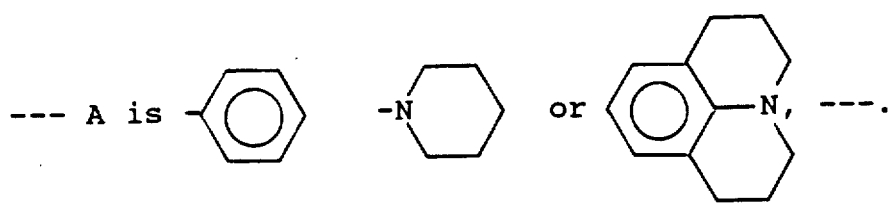

Column 109, line 59; after "hydrogen" insert a comma.

Signed and Sealed this

Twenty-fourth Day of September, 1991

Attest:

HARRY F. MANBECK, JR.

Attesting Officer

Commissioner of Patents and Trademarks